US011471467B2

(12) United States Patent
Rodríguez Villar et al.

(10) Patent No.: US 11,471,467 B2
(45) Date of Patent: Oct. 18, 2022

(54) RUTHENIUM COMPLEXES FOR TREATING CANCER WHICH COMPRISES CANCER STEM CELLS

(71) Applicants: UNIVERSIDADE DE SANTIAGO DE COMPOSTELA, a Coruña (ES); UNIVERSIDAD AUTÓNOMA DE MADRID, Madrid (ES)

(72) Inventors: Jessica Rodríguez Villar, Santiago de Compostela (ES); José Luis Mascareñas Cid, Santiago de Compostela (ES); José Rodríguez Couceiro, Santiago de Compostela (ES); Jesús Mosquera Mosquera, Santiago de Compostela (ES); Marcos Eugenio Vázquez Sentís, Santiago de Compostela (ES); Bruno Sainz Anding, Madrid (ES)

(73) Assignees: UNIVERSIDADE DE SANTIAGO DE COMPOSTELA; UNIVERSIDAD AUTÓNOMA DE MADRID

( * ) Notice: Subject to any disclaimer, the term of this patent is extended or adjusted under 35 U.S.C. 154(b) by 0 days.

(21) Appl. No.: 16/348,589

(22) PCT Filed: Nov. 10, 2017

(86) PCT No.: PCT/ES2017/070745
§ 371 (c)(1),
(2) Date: May 9, 2019

(87) PCT Pub. No.: WO2018/087413
PCT Pub. Date: May 17, 2018

(65) Prior Publication Data
US 2020/0054647 A1 Feb. 20, 2020

(30) Foreign Application Priority Data
Nov. 10, 2016 (ES) ................ ES201631426

(51) Int. Cl.
*A61P 35/00* (2006.01)
*A61K 31/555* (2006.01)

(52) U.S. Cl.
CPC ............ *A61K 31/555* (2013.01); *A61P 35/00* (2018.01)

(58) Field of Classification Search
CPC combination set(s) only.
See application file for complete search history.

(56) References Cited

U.S. PATENT DOCUMENTS 9,255,118 B2   2/2016   Bonnet

FOREIGN PATENT DOCUMENTS

WO   2012052821 A1   4/2012

OTHER PUBLICATIONS

Siewert et al., "Chemical Swarming: Depending on Concentration, an Amphiphilic Ruthenium Polypyridyl Complex Induces Cell Death via Two Different Mechanisms," Bioinorganic Chemistry, published online Jul. 4, 2016.*
Huang et al., "Synthesis, characterization and biological evaluation of labile intercalative ruthenium(II) complexes for anticancer drug screening," Dalton Trans., 2016, 45, 13135-13145 (published May 2016).*
Goldbach, R.E., et al.; "N-Acetylmethionine and biotin as photocleavable protective groups for ruthenium polypyridyl complexes," Chemistry European Journal, 2011, pp. 9924-9929, vol. 17.
Ying, Liu, et al.; "Stabilization for loop isomers of c-myc G-quadruplex DNA and anticancer activity by ruthenium complexes," MedChemCommun., 2014, pp. 1724-1728, vol. 5.
Y an Y Wm Ongkeko; "ABCG2: the key to chemoresistance in cancer stem cells," Expert Opinion Drug Metab. Toxicol., 2009, pp. 1529-1542. vol. 5, DOI: 10.1517/17425250903228834; http://www.ncbi.nlm.nih.gov/pubmed/19708828.
Wei Mo, et al.; "Human ABCG2:structure, function and its role in multidrug resistance," International J. Biochem. Molecular Biology, 2012, pp. 1-27, vol. 3.
He, Lei, et al.; "Octahedral Ruthenium Complex Selectively Stabilizes G-quadruplexes," Chem. Commun., 2016, DOI: 10.1039/C6CC03117J.
International Search Report, dated Feb. 8, 2018.
Extended European Search Report, European Patent Application No. 17869235.6, dated Jun. 30, 2020.
Telbisz, Ágnes, et al.; "Effects of the lipid environment, cholesterol and bile acids on the function of the purified and reconstituted human ABCG2 protein," Biochem. J., 2013, vol. 450, pp. 387-395; doi: 10.1042/BJ20121485.
Gorle, Anil K., et al.; "Multinuclear ruthenium(II) complexes as anticancer agents," New J. Chem., 2014, vol. 38, pp. 4049-4059.
Bahreman, Azadeh, et al.,; Yellow-light sensitization of ligand photosubstitution action in a ruthenium polypyridyl complex covalently bound to a rhodamine dye, Dalton Trans., 2014, vol. 43, pp. 4494-4505.

(Continued)

*Primary Examiner* — Jared Barsky
(74) *Attorney, Agent, or Firm* — Tristan A. Fuierer; Casimir Jones, S.C.

(57) ABSTRACT

The present invention relates to the use of ruthenium(II) complexes for preparing a medicinal product for treating cancer, particularly cancer comprising cancer stem cells. Said ruthenium complexes are capable of selectively metallating guanine quadruplexes, thus resulting in increased expression of the c-MYC oncogene. This increase in the proportion of c-MYC may promote the differentiation of cancer stem cells.

23 Claims, 23 Drawing Sheets
Specification includes a Sequence Listing.

(56) References Cited

OTHER PUBLICATIONS

Cheng, Chien-Chung, et al.; "Covalent Interaction of Ru(terpy)(tmephen)Cl+ with DNA: A Potential Ruthenium-Based Anticancer Drug," Journal of the Chinese Chemical Society, 2000, vol. 47, pp. 213-220.
Lameijer, Lucien N., et al.; "D-Versus L-Glucose Conjugation: Mitochondrial targeting of a Light-Activated Dual-Mode-of-Action Ruthenium-based Anticancer Prodrug," Chem. Eur. J , 2016, vol. 22, pp. 18484-18491.
Rodríguez, Jéssica, et al.; "Ruthenation of Non-stacked Guanines in DNA G-Quadruplex Structures: Enchancement of a c-MYC Expression," Agnew. Chem., 2016, vol. 128, pp. 15844-15847.
JP Office Action for JP Patent Application No. 2019-524182 drafted Aug. 30, 2021, dated Sep. 3, 2021.
Matsumura and Y. Kanakura, Cancer Stem Cells as a Target of Molecular Therapeutics, Biotherapy, 21(4), 209-16, 2007, Abstract Only.

\* cited by examiner

SEQUENCE LISTING

```
<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
ttgagggtgg gtagggtggg taaa                                            24

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
ctgaggagga acaagaagat gag                                             23

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
tgtgaggagg tttgctgtg                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
gtttggagca atcaccttcg                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
accctccaac acaacaacag                                                 20

<210> SEQ ID NO 6
<211> LENGTH: 23
<212> TYPE: DNA
<213> ORGANISM: Artificial Sequence
```

```
<220> FEATURE:
<223> OTHER INFORMATION: Synthetic Construct

<400> SEQUENCE: 6
ggtgtgaacc atgagaagta tga                                    23

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
gagtccttcg atcaccacaa ag                                     22
```

RUTHENIUM COMPLEXES FOR TREATING CANCER WHICH COMPRISES CANCER STEM CELLS

CROSS-REFERENCE TO RELATED APPLICATIONS

This application is filed under the provisions of 35 U.S.C. § 371 and claims the priority of International Patent Application No. PCT/Es2017/070745 filed on 10 Nov. 2017 entitled "RUTHENIUM COMPLEXES FOR TREATING CANCER WHICH COMPRISES CANCER STEM CELLS" in the name of Jessica RODRÍGUEZ VILLAR, et al., which claims priority to Spanish Patent Application No. P201631426, filed on 10 Nov. 2016, both of which are hereby incorporated by reference herein in their entirety.

FIELD OF THE INVENTION

The present invention relates to the use of ruthenium complexes or of pharmaceutical compositions containing same for treating cancer comprising cancer stem cells.

BACKGROUND OF THE INVENTION

It is known that metallic compounds containing platinum exhibit significant anti-tumor activities. The most well-known of these metallic compounds is cisplatin, which is used today in the clinical treatment of various cancers.

Nevertheless, anti-tumor treatment based on compounds of this type often leads to severe side effects. Therefore, there is a major interest in developing metallic compounds with anti-tumor activity that are more selective and less toxic than cisplatin. In this sense, ruthenium complexes are a promising alternative due to their kinetic stability and their redox and photochemical properties. Ruthenium complexes which recognize in a non-covalent manner double-stranded DNA and also form covalent adducts with the DNA have been described. Most of these complexes bind to the two strands of the DNA. However, due to the functional relevance of guanine quadruplexes (GQs), it would be of great interest to develop complexes capable of acting by means of binding to these structures. In this sense, Wu et al., Inorg. Chem. 2013, 2, 11332 describe ruthenium complexes capable of covalently metallating a GQ structure, however this reaction is rather non-selective.

In relation to tumor development and the onset of metastasis, a population of cells called "cancer stem cells" capable of differentiating into different cell types and self-renewal has recently been identified, so it is considered likely that these cells are related to relapse processes after anti-tumor treatment and to the onset of metastasis. Therefore, it is of great interest to provide new anti-tumor therapies capable of acting on this cell type.

Another challenge in the treatment of cancer consists of achieving targeted therapies which allow delivering the active compound selectively to the site of action, thereby reducing the required dose, and allow specifically acting on cancer cells, preventing normal cells from being damaged.

There is therefore a need to provide alternative methods for treating cancer which allow solving the deficiencies of the state of the art.

SUMMARY OF THE INVENTION

The inventors have discovered that ruthenium(II) complexes as defined herein are capable of selectively metallating unpaired guanines present in parallel guanine quadruplexes (GQs). As has been observed, this selective metallation causes an increase in the expression of the c-MYC oncogene, which is involved in many cellular processes. Additionally, the inventors have found that this increase in the proportion of c-MYC may promote the differentiation of cancer stem cells, which makes these ruthenium complexes an important tool in biology and medicine. It has furthermore been observed that metallation reaction increases by a greater or lesser degree depending on the type of complex when irradiated with light.

Taking this into account, in a first aspect the present invention relates to a ruthenium complex of formula (I)

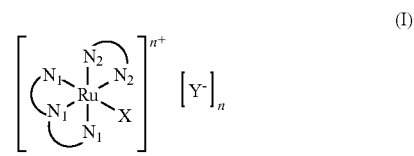

wherein
$N_1$—$N_1$—$N_1$ represents an N,N,N-tridentate aza-aromatic ligand;
$N_2$—$N_2$ represents an N,N-bidentate aza-aromatic ligand;
X is selected from $OH_2$, Cl, Br, I, and $SR_1R_2$;
$R_1$ and $R_2$ are independently selected from optionally substituted $C_1$-$C_{12}$ alkyl;
$Y^-$ is a monovalent anion; and
n is 1 or 2;
for preparing a medicinal product for treating cancer comprising cancer stem cells.

In a second aspect, the present invention relates to a pharmaceutical composition or a medicinal product comprising a ruthenium complex of formula (I) as defined herein for use thereof in the treatment of cancer comprising cancer stem cells.

In a third aspect, the invention relates to a method for treating cancer comprising cancer stem cells, which method comprises administering a therapeutically effective amount of a ruthenium complex of formula (I) as defined herein and irradiating with light.

In another aspect, the invention relates to a conjugate comprising:
a ruthenium complex of formula (I), and
an ABCG2 substrate.

In another aspect, the invention relates to a conjugate comprising:
a ruthenium complex of formula (I), and
an anti-tumor drug.

Other aspects of the invention relate to the conjugates of the invention for use thereof in medicine and for use thereof in the treatment of cancer comprising cancer stem cells. Finally, another aspect of the invention relates to a method for treating cancer comprising cancer stem cells, which method comprises administering a therapeutically effective amount of a conjugate as defined herein and irradiating with light.

DETAILED DESCRIPTION OF THE INVENTION

Figure 1:
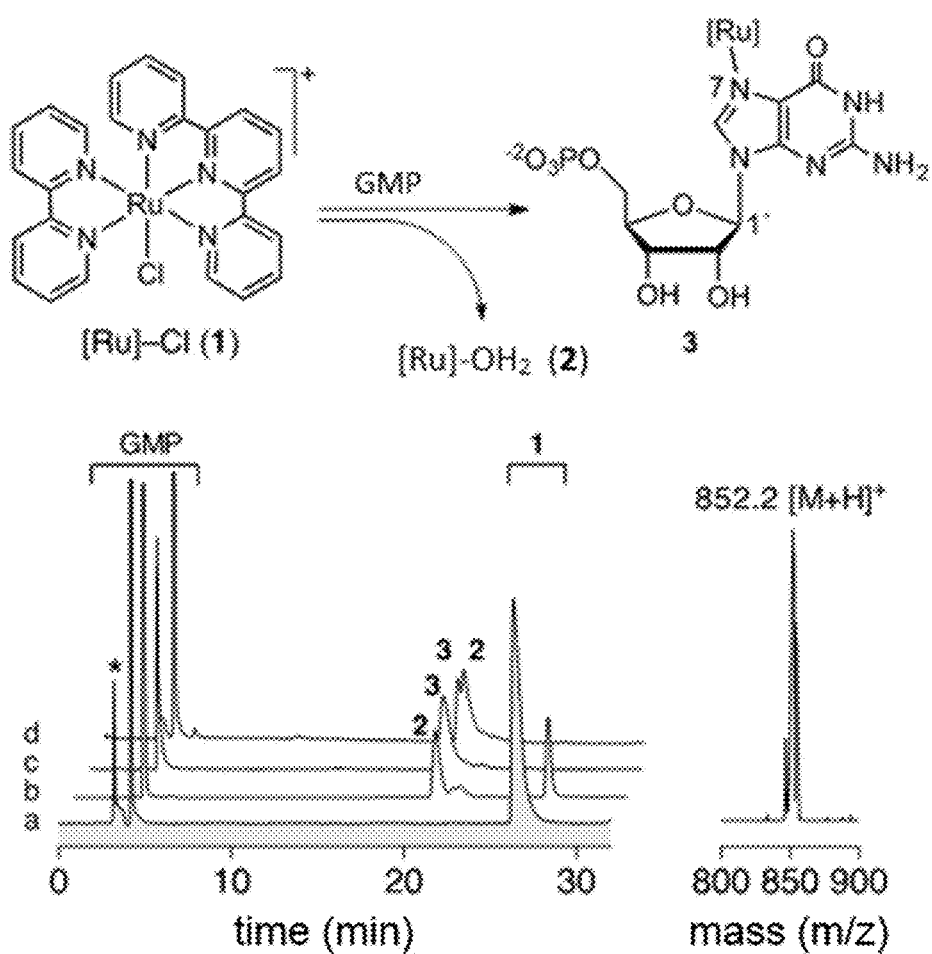
FIG. 1. (Top) Metallation reaction of GMP with complex 1 and formation of aquo 2 derivative. (Bottom left) HPLC of the reaction of complex 1 (250 µM) and GMP (750 µM) in 10 mM phosphate buffer (pH=7.5) and 100 mM NaCl: (a) in the dark at t=0; (b) after 30 min in the dark; (c) initial mixture after 30 min of irradiation at 455 nm; (d) initial mixture after 2 h in the dark. (Bottom right) Mass spectrum of monoadduct 3.

Researchers have found that ruthenium complexes of formula (I) wherein X is Cl are capable of selectively metallating guanosine monophosphate (GMP) by means of prior transformation into the active aquo complex (X=H$_2$O). This reaction can be accelerated by means of irradiation with light.

It has also been observed that these complexes cause an increase in the expression levels of the c-MYC oncogene, therefore acting as transcription activators. In the case of ruthenium complexes wherein X is selected from SR$_1$R$_2$, these complexes are stable in the dark, but the thioether ligand can be readily interchanged by means of irradiation with light, giving rise to the active aquo complex. In that case, it has been confirmed that the ruthenium complexes wherein X is selected from SR$_1$R$_2$ are completely inert in the absence of light, but cause an increase in c-MYC levels after irradiation with light. It has been furthermore confirmed that in the case of the ruthenium complexes of the invention wherein X is H$_2$O (an aquo complex), it is possible to increase the c-MYC oncogene levels both in the dark and by means of irradiation with light.

In a first aspect, the invention relates to an Ru(II) complex of formula (I)

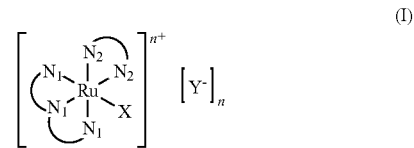

wherein
N$_1$—N$_1$—N$_1$ represents an N,N,N-tridentate aza-aromatic ligand;
N$_2$—N$_2$ represents an N,N-bidentate aza-aromatic ligand;
X is selected from OH$_2$, Cl, Br, I, and SR$_1$R$_2$;
R$_1$ and R$_2$ are independently selected from optionally substituted C$_1$-C$_{12}$ alkyl;
Y$^-$ is a monovalent anion; and
n is 1 or 2;
for preparing a medicinal product for treating cancer comprising cancer stem cells.

Ruthenium Complexes

The term "alkyl" refers to a linear or branched alkane derivative which contains from 1 to 12 ("$C_1$-$C_{12}$ alkyl"), preferably from 1 to 6 ("$C_1$-$C_6$ alkyl"), more preferably from 1 to 3 ("$C_1$-$C_3$ alkyl"), carbon atoms and is bound to the rest of the molecule through a single bond. Illustrative examples of alkyl groups include methyl, ethyl, n-propyl, i-propyl, n-butyl, i-butyl, t-butyl, pentyl, hexyl.

The term "alkenyl" refers to a linear or branched hydrocarbon chain radical which contains from 2 to 6 ("$C_2$-$C_6$ alkenyl"), more preferably from 2 to 3 ("$C_2$-$C_3$ alkenyl"), carbon atoms, contains at least one double bond, and is bound to the rest of the molecule by means of a single bond. Illustrative examples include ethenyl, propenyl, allyl, butenyl, 1-methyl-2-buten-1-yl, and the like.

The term "alkynyl" refers to a linear or branched hydrocarbon chain radical which contains from 2 to 6 ("$C_2$-$C_6$ alkynyl"), more preferably from 2 to 3 ("$C_2$-$C_3$" alkynyl), carbon atoms, contains at least one triple bond, and is bound to the rest of the molecule by means of a single bond. Illustrative examples include ethynyl, propinyl, butynyl, and the like.

The term "aryl" refers to an aromatic group having between 6 and 14, preferably between 6 and 10, carbon atoms, comprising 1 or 2 aromatic nuclei condensed with one another. Illustrative examples of aryl groups include phenyl, naphthyl, indenyl, phenanthryl, etc.

The term "heterocyclyl" refers to a monocyclic or bicyclic system which can be completely or partially saturated or aromatic ("heteroaryl") containing from 3 to 10, preferably from 5 to 10, more preferably from 5 to 7, ring atoms containing one or more, specifically one, two, three, or four ring heteroatoms independently selected from N, O, and S, and with the remaining ring atoms being carbon.

The term "halogen" refers to bromine, chlorine, iodine, or fluorine.

The term N,N-bidentate or N,N,N-tridentate aza-aromatic ligand refers to aromatic molecules which can take up two (bidentates) or three (tridentates) coordination sites of the Ru(II) metal center by means of coordination through nitrogen atoms alone. Preferably, this aromatic molecule is a stable heteroaryl having from 10 to 32, preferably from 12 to 28, more preferably from 12 to 20, members (bidentate) or having from 15 to 32, preferably from 18 to 30, more preferably from 18 to 26, members (tridentate), formed by carbon atoms and from two (bidentate) or three (tridentate) up to six, preferably 2, 3, 4, or 5, nitrogen atoms. As it is used herein, the expression "heteroaryl having from 10 to 32 members or having from 15 to 32 members" means a heteroaryl group having a backbone from 10 to 32 atoms or from 15 to 32 atoms. For the purposes of this invention, the heterocycle can be a polycyclic ring system which can include fused or condensed ring systems. Examples of N,N-bidentate and N,N,N-tridentate aza-aromatic ligands include, but are not limited to, 2,2'-bipyridine, 2,2'-bipyrazine, 2,2'-bipyrimidine, 1,10-phenanthroline, bathophenanthroline, 2,2'-bisquinoline, 1,1'-bisisoquinoline, 2-pyridinyl-2-quinoline, 3-pyridinyl-2-quinoline, 1-pyridinyl-2-isoquinoline, 2-pyridinyl-2-[1,8]-naphthyridine, 2,2': 6',2''-terpyridine, 2,6-bis(2'-benzimidazoly)pyridine, 2,6-bis (8'-quinolinyl)pyridine, 2,6-bis(2'-[1,8]-naphthyridinyl) pyridine, 2-pyridinyl-2-[1,10]-phenanthroline, 2-quinolinyl-8-[1,10]-phenanthroline, and the like. These aza-aromatic ligands can be optionally substituted.

The aforementioned groups can be optionally substituted in one or more available positions with one or more suitable groups such as OR, SR, SOR, $SO_2R$, $OSO_2R$, $SO_3R$, $SO_3^-$ $Z^+$, $NO_2$, $N(R)_2$, N(R) COR, N(R) $SO_2R$, CN, halogen, COR, $CO_2R$, $CO_2^-Z^+$, OCOR, $OCO_2R$, OCONHR, OCON $(R)_2$, CONHR, $CON(R)_2$, $C_1$-$C_6$ alkyl, $C_2$-$C_6$ alkenyl, $C_2$-$C_6$ alkynyl, $C_6$-$C_{14}$ aryl, and 3- to 10-membered heterocyclyl, wherein each of the groups R is independently selected from the group consisting of hydrogen, $C_1$-$C_6$ alkyl, $C_2$-$C_6$ alkenyl, $C_2$-$C_6$ alkynyl, $C_6$-$C_{14}$ aryl, and 3- to 10-membered heterocyclyl, and where Z is preferably an inorganic monovalent cation, such as a sodium or potassium cation, for example. In a particular embodiment, between 1 to 5 aza-aromatic ligands in a compound of formula (I), preferably 2 or 3, are substituted in the para position by a sulfonate ($SO_3^-Z^+$) or carboxylate ($CO_2^-Z^+$) group.

In the present document, "monovalent anion" refers to an inorganic or organic anion with a single negative charge which can form an ionic bond with a cation of a Ru(II) complex. Preferably, the monovalent anion is inorganic. Examples of monovalent anions include $PF_6^-$, $Cl^-$, $Br^-$, $I^-$, $F^-$, $BF_4^-$, $CF_3SO_3^-$, $CH_3SO_3^-$, $CH_3C_6H_4SO_3NO_3^-$, $NO_2^-$, $SCN^-$, $BrO_3^-$, $IO_3^-$, $HCO_3^-$, $HCOO^-$, $CH_3COO^-$, $CF_3CO_2^-$, $HSO_4^-$, $HSO_3^-$, and $H_2PO_3^-$.

In a particular embodiment, $N_1$—$N_1$—$N_1$ is an N,N,N-tridentate aza-aromatic ligand selected from the group consisting of optionally substituted 2,2':6',2''-terpyridine, 2,6-bis(2'-benzimidazoly)pyridine, 2,6-bis(8'-quinolinyl) pyridine, 2,6-bis(2'-[1,8]-naphthyridinyl)pyridine, 2-pyridinyl-2-[1,10]-phenanthroline, and 2-quinolinyl-8-[1, 10]-phenanthroline.

In one embodiment, $N_1$—$N_1$—$N_1$ is selected from the group consisting of:

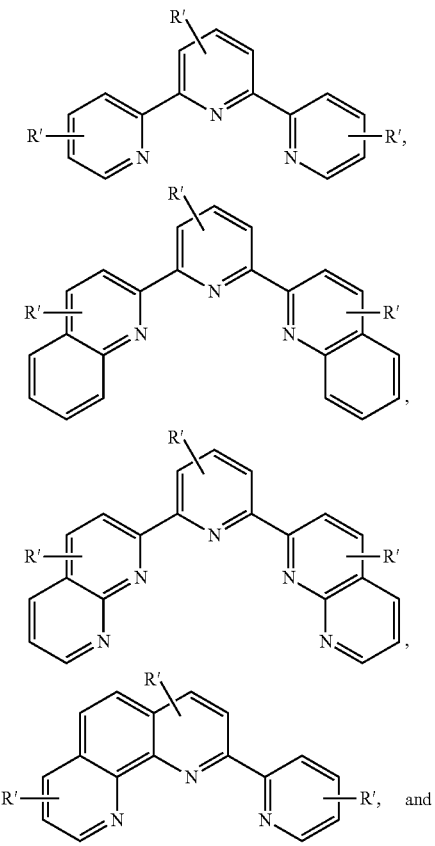

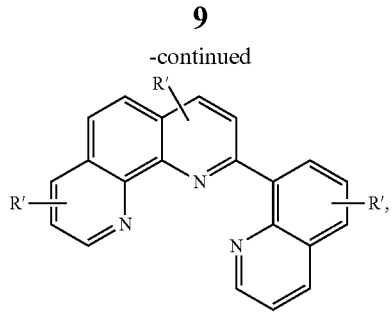

wherein each group R' is independently selected from hydrogen, optionally substituted $C_1$-$C_6$ alkyl, optionally substituted $C_6$-$C_{14}$ aryl, optionally substituted 5- to 10-membered heteroaryl, and halogen. Preferably, each group R' is independently selected from hydrogen, halogen, sulfonate, carboxylate, unsubstituted $C_1$-$C_6$ alkyl, unsubstituted $C_6$-$C_{14}$ aryl, and unsubstituted 5- to a 10-membered heteroaryl. More preferably, each group R' is independently selected from hydrogen, Cl, Br, methyl, ethyl, n-propyl, i-propyl, n-butyl, and t-butyl. In a particular embodiment, each group R' is hydrogen.

According to a particular embodiment, $N_1$—$N_1$—$N_1$ is selected from the group consisting of:

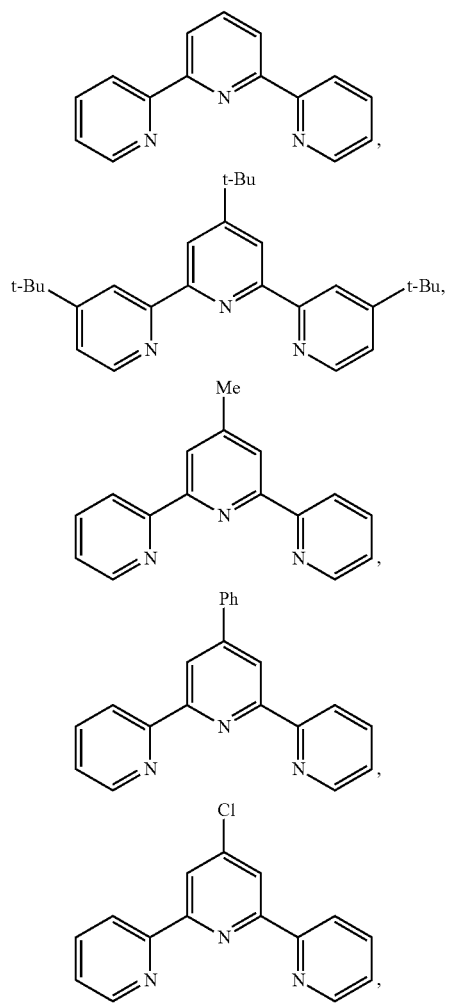

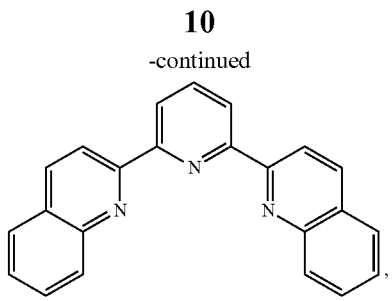

In another embodiment, $N_1$—$N_1$—$N_1$ represents optionally substituted 2,2':6',2''-terpyridine. Preferably, $N_1$—$N_1$—$N_1$ is selected from 2,2':6',2''-terpyridine optionally substituted with $C_1$-$C_6$ alkyl, $C_6$-$C_{14}$ aryl, 5- to 10-membered heteroaryl, sulfonate, carboxylate, or halogen; more preferably 2,2':6',2''-terpyridine optionally substituted with Cl, Br, sulfonate, carboxylate, methyl, ethyl, n-propyl, i-propyl, n-butyl, and t-butyl. In a particular embodiment, $N_1$—$N_1$—$N_1$ represents 2,2':6',2''-terpyridine.

According to a particular embodiment of the invention, $N_2$—$N_2$ is an N,N-bidentate aza-aromatic ligand selected from the group consisting of optionally substituted 2,2'-bipyridine, 2,2'-bipyrazine, 2,2'-bipyrimidine, 1,10-phenanthroline, bathophenanthroline, 2,2'-bisquinoline, 1,1'-bisisoquinoline, 2-pyridinyl-2-quinoline, 3-pyridinyl-2-quinoline, 1-pyridinyl-2-isoquinoline, and 2-pyridinyl-2-[1,8]-naphthyridine.

In one embodiment, $N_2$—$N_2$ is selected from the group consisting of:

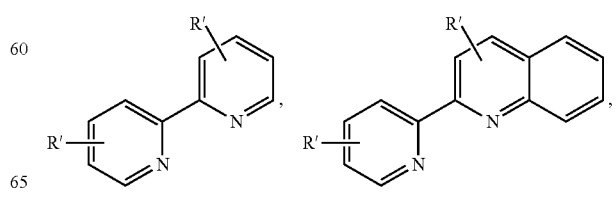

-continued

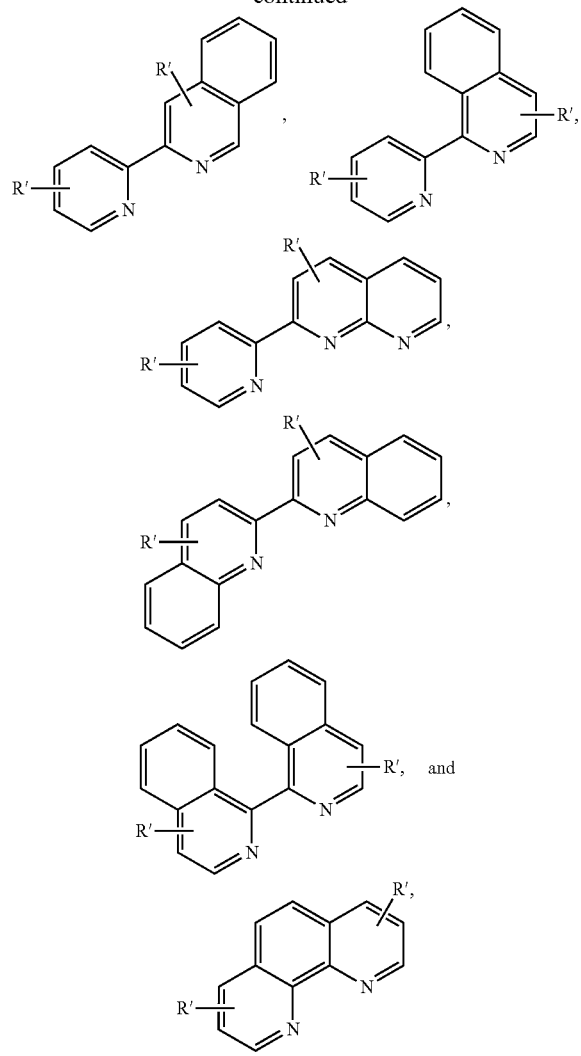

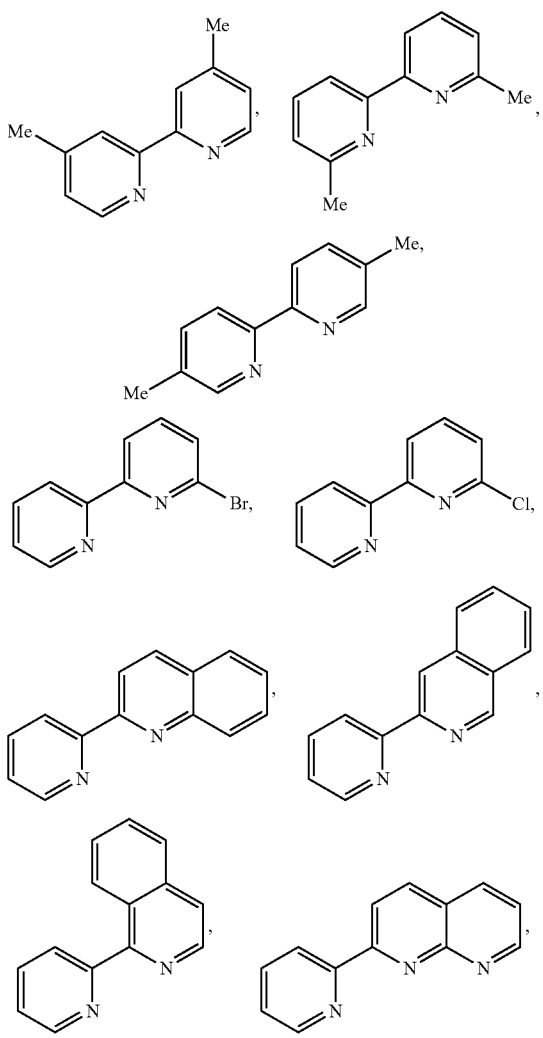

wherein each group R' is independently selected from hydrogen, sulfonate, carboxylate, optionally substituted $C_1$-$C_6$ alkyl, optionally substituted $C_6$-$C_{14}$ aryl, optionally substituted 5- to 10-membered heteroaryl, and halogen. Preferably, each group R' is independently selected from hydrogen, halogen, unsubstituted $C_1$-$C_6$ alkyl, unsubstituted $C_6$-$C_{14}$ aryl, and unsubstituted 5- to 10-membered heteroaryl. More preferably, each group R' is independently selected from hydrogen, Cl, Br, sulfonate, carboxylate, methyl, ethyl, n-propyl, i-propyl, n-butyl, and t-butyl. In a particular embodiment, each group R' is hydrogen.

According to a particular embodiment, $N_2$—$N_2$ is selected from the group consisting of:

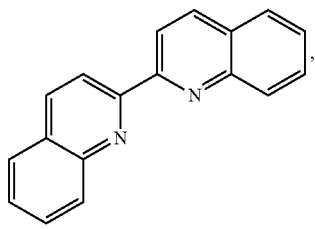

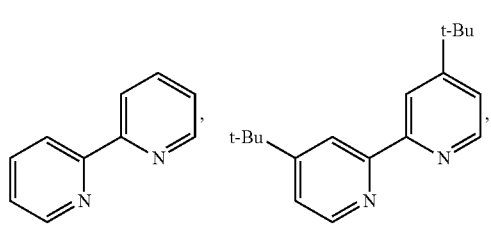

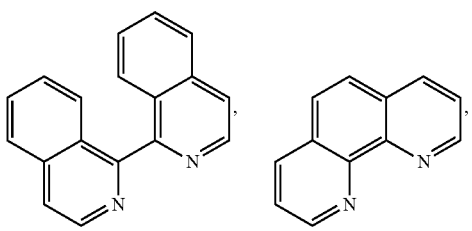

-continued

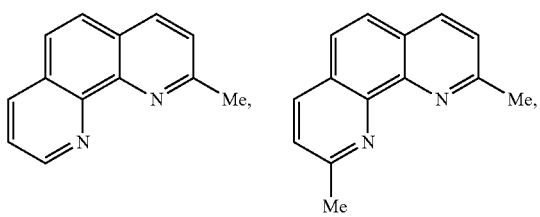

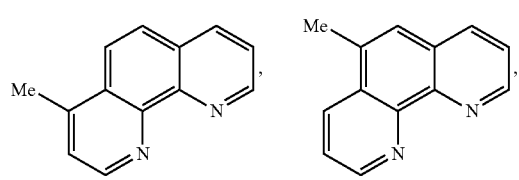

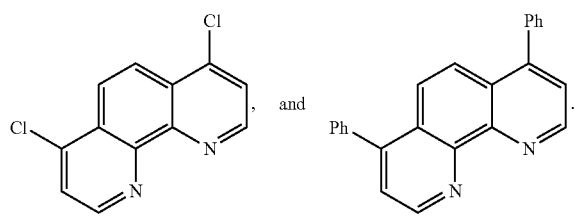

In another embodiment, $N_2$—$N_2$ represents optionally substituted 2,2'-bipyridine. Preferably, $N_2$—$N_2$ is selected from 2,2'-bipyridine optionally substituted with $C_1$-$C_6$ alkyl, $C_6$-$C_{14}$ aryl, 5- to 10-membered heteroaryl, sulfonate, carboxylate, or halogen; more preferably 2,2'-bipyridine optionally substituted with Cl, Br, sulfonate, carboxylate, methyl, ethyl, n-propyl, i-propyl, n-butyl, and t-butyl. In a particular embodiment, $N_2$—$N_2$ represents 2,2'-bipyridine.

According to an embodiment of the invention, $N_1$—$N_1$—$N_1$ represents

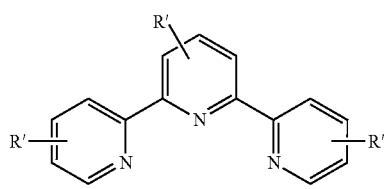

and $N_2$—$N_2$ represents

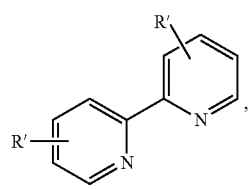

where each group R' is independently selected from hydrogen, sulfonate, carboxylate, optionally substituted $C_1$-$C_6$ alkyl, optionally substituted $C_6$-$C_{14}$ aryl, optionally substituted 5- to 10-membered heteroaryl, and halogen.

In a particular embodiment, the Ru(II) complex has the following formula:

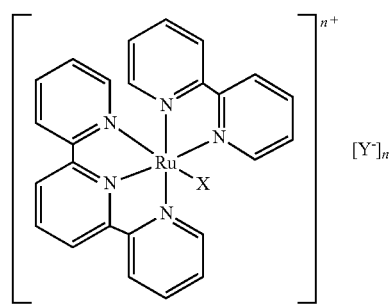

wherein X, Y⁻, and n are as defined herein.

The value of n is determined by the chemical structure and electric charge of the selected ligands and the 2+ electric charge of the central Ru(II) atom. Therefore, when X represents $OH_2$ or $SR_1R_2$, then n is 2. When X represents Cl, Br, or I, then the value of n is 1. The complex of formula (I) is neutral, i.e., it has a zero overall charge.

In a particular embodiment, X represents $OH_2$. Preferably, $N_1$—$N_1$—$N_1$ represents optionally substituted 2,2':6',2"-terpyridine as defined above, $N_2$—$N_2$ represents optionally substituted 2,2'-bipyridine as defined above, and X represents $OH_2$.

In another particular embodiment, X represents Cl, Br, or I, preferably Cl. In a particular embodiment, $N_1$—$N_1$—$N_1$ represents optionally substituted 2,2':6',2"-terpyridine as defined above, $N_2$—$N_2$ represents optionally substituted 2,2'-bipyridine as defined above, and X represents Cl, Br, or I, preferably Cl.

In one embodiment, X represents $SR_1R_2$, where $R_1$ and $R_2$ are independently selected from optionally substituted $C_1$-$C_{12}$ alkyl. Preferably, $R_1$ and $R_2$ are independently selected from $C_1$-$C_{12}$ alkyl, preferably $C_1$-$C_6$ alkyl optionally substituted with one or more groups selected from halogen, OR", N(R")$_2$, N(R")COR", CN, $NO_2$, COR", $CO_2$R", OCOR", $OCO_2$R", OCONHR", OCON(R")$_2$, CONHR", CON(R")$_2$, $C_1$-$C_6$ alkyl, $C_2$-$C_6$ alkenyl, $C_2$-$C_6$ alkynyl, $C_6$-$C_{14}$ aryl, and 3- to 10-membered heterocyclyl, where each group R" is independently selected from the group consisting of hydrogen, $C_1$-$C_6$ alkyl, $C_2$-$C_6$ alkenyl, $C_2$-$C_6$ alkynyl, $C_6$-$C_{14}$ aryl, and 3- to 10-membered heterocyclyl. More preferably, $R_1$ and $R_2$ are independently selected from $C_1$-$C_6$ alkyl optionally substituted with one or more groups selected from OR", N(R")COR", and $CO_2$R", where each group R" is independently selected from hydrogen, $C_1$-$C_6$ alkyl, $C_2$-$C_6$ alkenyl, $C_2$-$C_6$ alkynyl, $C_6$-$C_{14}$ aryl, and 3- to 10-membered heterocyclyl. More preferably, $R_1$ and $R_2$ are independently selected from $C_1$-$C_6$ alkyl optionally substituted with one or more groups selected from OH, N(H)COCH$_3$, and $CO_2$H. In one embodiment, $R_1$ and $R_2$ are independently selected from $CH_3$, $CH_2CH_2OH$, and $CH_2CH_2CH(COOH)N(H)COCH_3$.

In an embodiment of the invention, the ruthenium complex is selected from the group consisting of:

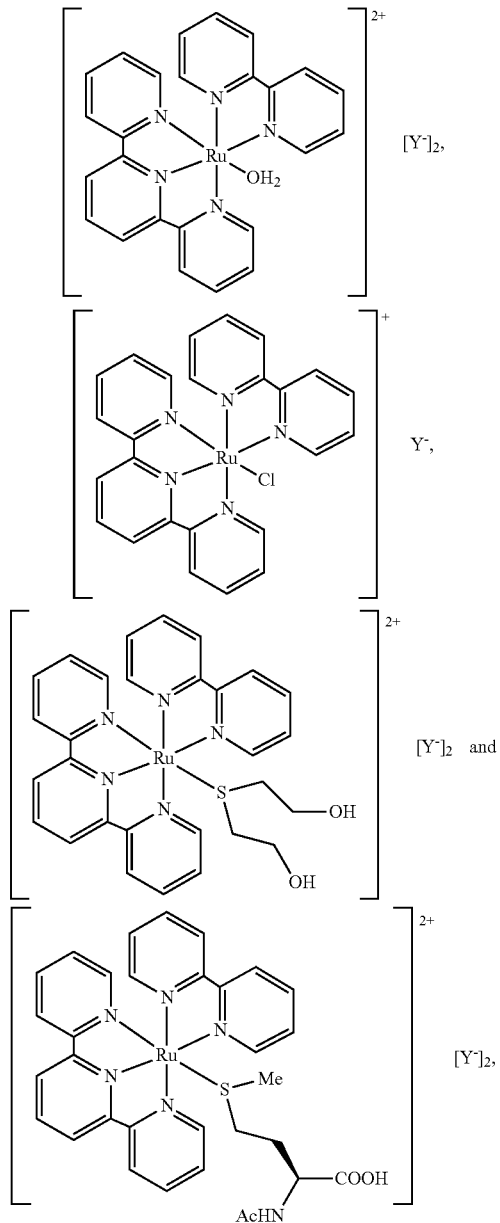

wherein Y⁻ is as defined herein.

In a particular embodiment, Y⁻ is selected from the group consisting of $PF_6^-$, $Cl^-$, $Br^-$, $I^-$, $F^-$, $BF_4^-$, $CF_3SO_3-$, $CH_3SO_3-$, $CH_3C_6H_4SO_3NO_3-$, $NO_2^-$, $SCN^-$, $BrO_3^-$, $IO_3^-$, $HCO_3^-$, $HCOO^-$, $CH_3COO^-$, $HSO_4^-$, $HSO_3^-$, and $H_2PO_3^-$. Preferably, Y⁻ is selected from the group consisting of $PF_6^-$, $Cl^-$, Br, $BF_4^-$, $CF_3SO_3-$, $CH_3SO_3-$, and $CH_3C_6H_4SO_3^-$. In one embodiment, Y— is $Cl^-$ or $PF_6^-$, preferably $PF_6^-$.

The ruthenium complexes of the present invention can be obtained by means of methods known by one skilled in the art, for example, by means of the methods mentioned in the example of this document or modifications thereof known by one skilled in the art.

Conjugates Consisting of the Ru Complex and an ABCG2 Substrate

The inventors have observed that the binding of the ruthenium complex to an ABCG2 substrate, such as riboflavin, for example, allows targeting the ruthenium complexes to cancer stem cells.

Therefore, in another aspect the invention relates to a conjugate comprising:
a ruthenium complex of formula (I), and
an ABCG2 substrate.

As it is used herein, "ABCG2" refers to a member of the superfamily of ATP transporters which is known to contribute to multiple drug resistance (MDR) in cancer chemotherapy. The protein sequence encoded by the ABCG2 gene in humans corresponds with the sequence with accession number Q9UNQ0 in the Uniprot database dated 5 Nov. 2016.

As it is used herein, "ABCG2 substrate" refers to a compound which can be transported by the ABCG2 transporter, particularly hydrophilic conjugated anions, more particularly sulfated anions or hydrophobic molecules. One skilled in the art will be able to identify if a compound is an ABCG2 substrate, for example, by means of using an ATPase assay using Sf9 membranes or in an essay shown in Glavinas H. et al., Drug Metab Dispos. 2007 September; 35(9):1533-42

In a particular embodiment, the ABCG2 substrate is a tyrosine kinase inhibitor such as imatinib and gefitinib, flavopiridol and the camptothecins topotecan, irinotecan, and the active metabolite SN-38 thereof [7-ethyl-10-hydroxy-camptothecin], or mitoxantrone. Other substrates include drugs such as cimetidine, prazosin, statins, and zidovudine. Additionally, other ABCG2 substrates are estrone, 17β estradiol, porphyrins such as heme, protoporphyrin IX, and 2-amino-1-methyl-6-phenylimidazo[4,5-b] pyridine. In another embodiment, the ABCG2 substrate is a chemotherapeutic agent such as amsacrine, asparaginase, azathioprine, bisantrene, bleomycin, busulfan, capecitabine, carboplatin, carmustine, chlorambucil, cisplatin, cladribine, clofarabine, cyclophosphamide, cytarabine, dacarbazine, dactinomycin, daunorubicin, docetaxel, doxorubicin, epirubicin, etoposide, flavopiridol, fludarabine, fluorouracil, gemcitabine, idarubicin, ifosfamide, irinotecan, hydroxyurea, leucovorin, liposomal daunorubicin, liposomal doxorubicin, lomustine, chlormethine, melphalan, mercaptopurine, mesna, methotrexate, mitomycin, mitoxantrone, oxaliplatin, paclitaxel, pemetrexed, pentostatin, procarbazine, satraplatin, streptozotocin, tegafur-uracil, temozolomide, teniposide, thioguanine, thiotepa, treosulfan, topotecan, vinblastine, vincristine, vindesine, SN-38, and vinorelbine.

In a particular embodiment, the ABCG2 substrate is a fluorescent compound. By way of non-limiting illustrative example, the fluorescent compound can be riboflavin, D-luciferin, rhodamine 123, pheophorbide a, BODIPY-prazosin, Hoechst 33342. In an even more preferred embodiment, the fluorescent ABCG2 substrate is riboflavin. As it is used herein, "riboflavin" refers to vitamin B2 with CAS number 83-88-5.

Preferably, the ruthenium complex and the ABCG2 substrate bind covalently to one another. The ruthenium complex and the ABCG2 substrate can be bound to one another directly, or alternatively through a linker or spacer. Therefore, in a particular embodiment the conjugate comprises a ruthenium complex of formula (I), an ABCG2 substrate, and a linker.

As it is used herein, the term "linker," also referred to as "spacer," refers to a chemical group or moiety which covalently binds to the ruthenium complex and ABCG2 substrate. It includes compounds comprising or deriving from divalent radicals, such as alkylene, arylene, or heteroarylene.

In a particular embodiment, the ruthenium complex and the ABCG2 substrate are bound together through a linker. In a particular embodiment, the linker is a hydrocarbon chain between 1 and 20, preferably between 1 and 10, more preferably between 1 and 6 atoms long, where one or more of the carbon atoms of the chain can be replaced with a heteroatom selected from NR', O, and S, where R' is selected from H, $C_1$-$C_6$ alkyl, and acetyl; and where one or more of the carbon atoms of the chain can be substituted by a substituent selected from =O, OH, SH, $NH_2$, COOH, $CH_3$, and Ph.

In a particular embodiment, the linker is an amino acid or a sequence of amino acids, preferably between 1 and 5 amino acids bound through peptide bonds. The term "amino acid" refers to compounds having an amino group and a carboxylic acid group and includes both natural amino acids and non-natural amino acids. The configuration of the amino acid can be L, D, or a racemic mixture.

One skilled in the art can determine the functional groups present in the linker and the way in which it binds to the ruthenium complex and the ABCG2 substrate, depending on the ruthenium complex and the ABCG2 substrate used. Preferably, the linker is bound to the ruthenium complex and the ABCG2 substrate by means of amide-, amine-, ether-, or ester-type bonds.

Preferably, the ruthenium complex in the conjugate is a complex of formula (I), wherein X is $SR_1R_2$, where $R_1$ and $R_2$ are as defined above. Once the conjugate is at the site of action or close to same, the active aquo complex (X=$OH_2$) can be released by means of irradiation with light as described herein. An inactive derivative that can be handled with ease and activated in a controlled manner at the desired actuation time and place can thereby be provided. In a particular embodiment, $SR_1R_2$ is methionine or a derivative thereof.

The term "methionine derivative" refers fundamentally to derivatives preferably substituted in the amino and/or carboxylic acid group of the methionine. Methionine derivatives include $C_1$-$C_6$ alkyl esters, acetates, amides, $C_1$-$C_6$ alkyl amines, and $C_1$-$C_6$ dialkyl amines of methionine.

In a preferred embodiment, the methionine derivative is a compound of formula:

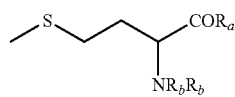

where
$R_a$ is selected from OH, $C_1$-$C_6$ O-alkyl, OAc, $NH_2$, NH—$C_1$-$C_6$ alkyl, N($C_1$-$C_6$ alkyl)$_2$, and NHAc; and
each $R_b$ is independently selected from H, $C_1$-$C_6$ alkyl, and Ac.

In one embodiment, the ruthenium complex is a complex of formula (I')

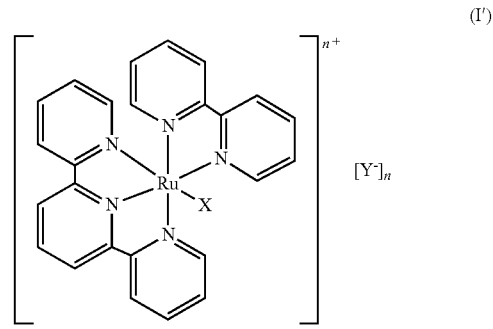

where X is $SR_1R_2$ as defined above, preferably X is methionine or a derivative thereof.

In a particular embodiment, the ruthenium complex is a complex of formula (I') where $SR_1R_2$ is methionine or a derivative thereof, preferably methionine, and is bound directly to the ABCG2 substrate, preferably through the amino group or the carboxylic acid group.

In another embodiment, the ruthenium complex is a complex of formula (I') where $SR_1R_2$ is methionine or a derivative thereof, preferably methionine, and is bound to the ABCG2 substrate by means of a linker, preferably through the amino group or the carboxylic acid group.

In a particular embodiment, the conjugate comprises:
a ruthenium complex of formula (I) wherein X is methionine,
riboflavin, and
optionally, a linker covalently bound to the methionine of the ruthenium complex and to riboflavin.

In one embodiment, the conjugate is:

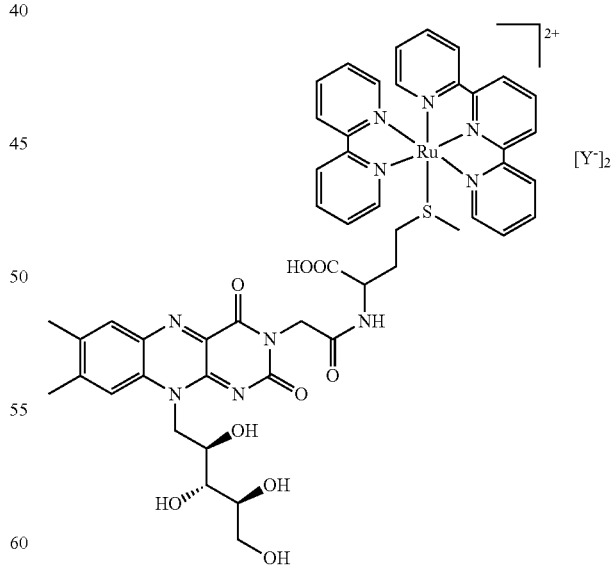

where Y is as defined above, preferably Y is $CF_3CO_2^-$.

The conjugate of the invention has various advantages. It allows precise transport of the active complex to the site of action, reducing the required dose, and allows selectively acting on cancer cells, preventing the attack on normal cells.

These conjugates can be obtained by means of conventional techniques known by one skilled in the art. If the ruthenium complex and the ABCG2 substrate do not contain functional groups suitable for chemically binding to one another, they can be derivatized to achieve the desired binding. Alternatively, the ruthenium complex and the ABCG2 substrate can be bound to one another (directly or after derivatization) through a bifunctional linker by means of reactions known by one skilled in the art.

Pharmaceutical Compositions

The Ru complexes and the conjugates of the invention can be used for preparing a pharmaceutical composition for treating cancer comprising cancer stem cells. Therefore, another aspect of the invention is a pharmaceutical composition comprising a ruthenium complex of formula (I) or a conjugate as defined herein, for use thereof in the treatment of cancer comprising cancer stem cells.

As it is used herein, the expression "pharmaceutical composition" refers to a formulation which has been adapted for administering a predetermined dose of one or more useful therapeutic agents to a cell, a group of cells, an organ, a tissue, or an organism.

The ruthenium complexes or the conjugates are administered in a therapeutically effective amount. A "therapeutically effective amount" is understood to be an amount which can provide a therapeutic effect and can be determined by one skilled in the art using means that are commonly used. The effective amount will vary with the particular disorder being treated, the age and physical condition of the subject being treated, the acuteness of the disorder, the duration of treatment, the nature of the simultaneous or combination therapy (if any), the specific route of administration, and similar factors within the knowledge and experience of the health professional. Generally, a maximum dose, i.e., the maximum safe dose according to reasonable medical judgment, is preferably used. For example, if the subject has a tumor, an effective amount can be the amount which reduces tumor load or volume (as determined, for example, by means of obtaining images of the tumor). Effective amounts can also be evaluated by means of the presence and/or frequency of cancer cells in blood or another body liquid or tissue (for example, a biopsy). If the tumor affects normal tissue or organ operation, then the effective amount can be evaluated by measuring the normal tissue or organ operation. Those skilled in the art will see that dosages can also be determined with the guidelines found in Goodman and Gilman's The Pharmacological Basis of Therapeutics, $9^{th}$ edition (1996), Annex II, pages 1707-1711 and in Goodman and Gilman's The Pharmacological Basis of Therapeutics, $10^{th}$ edition (2001), Annex II, pages 475-493.

The pharmaceutical compositions of the invention may include at least one pharmaceutically acceptable vehicle. As it is used herein, the term "pharmaceutically acceptable vehicle" means a filler, diluent, encapsulating material, or adjuvant for solid, semisolid, or liquid formulation, that is of any inert non-toxic type which is acceptable to the patient from a pharmacological/toxicological viewpoint and to the manufacturing pharmaceutical chemist from a physical/chemical viewpoint regarding composition, formulation, stability, patient acceptance, and bioavailability. Remington's Pharmaceutical Sciences, edited by Gennaro, Mack Publishing, Easton, Pa., 1995 describes various vehicles used in the formulation of pharmaceutical compositions and known techniques for preparing same. Some examples of materials that can be used as pharmaceutically acceptable vehicles include, but are not limited to, sugars such as lactose, glucose, and sucrose; starches such as corn starch and potato starch; cellulose and its derivatives such as sodium carboxymethylcellulose, ethylcellulose, and cellulose acetate; gum tragacanth powder; malt; gelatin; talc; excipients such as cocoa butter and suppository waxes; oils such as peanut oil, cottonseed oil, safflower oil, sesame oil, olive oil, corn oil, and soybean oil; glycols such as propyleneglycol; esters such as ethyl oleate and ethyl laurate; agar; detergents such as TWEEN™ 80; buffering agents such as magnesium hydroxide and aluminum hydroxide; alginic acid; pyrogen-free water; isotonic saline solution; Ringer's solution; ethyl alcohol; and phosphate buffer solutions, as well as other non-toxic compatible lubricants such as sodium lauryl sulfate and magnesium stearate; furthermore, coloring agents, release agents, coating agents, sweetening agents, flavoring agents and perfumes, preservatives, and antioxidants can also be present in the composition, according to the criterion of the one preparing the formulation. If filtration or other terminal sterilization methods are not viable, the formulations can be manufactured under aseptic conditions.

Pharmaceutical compositions of the invention include any solid composition (tablets, pills, capsules, granules, etc.), semi-solid composition (creams, salves, etc.), or liquid composition (solution, suspension, or emulsion).

The pharmaceutical compositions of this invention can be administered to a patient using any means known in the art including oral and parenteral routes. According to such embodiments, the compositions of the invention can be administered by means of injection (for example, intravenous, subcutaneous or intramuscular, intraperitoneal injection). In a particular embodiment, the ruthenium complexes or the conjugates of the invention are administered systemically, for example by means of i.v. infusion or injection. Injectable preparations, for example, sterile aqueous or oily injectable suspensions, can be formulated according to the known technique using suitable suspending agents and dispersing agents or wetting agents. The sterile injectable preparation can also be a sterile injectable solution, suspension, or emulsion in a non-toxic diluent or solvent, acceptable by means of parenteral route, for example, as a solution in 1,3-butanediol. The acceptable vehicles and solvents that can be used include, among others, water, Ringer's solution, U.S.P., and isotonic sodium chloride solution. Furthermore, sterile fixed oils are conventionally used as solvent or suspension medium. Any light fixed oil including synthetic mono- or diglycerides can be used for this purpose. Furthermore, fatty acids such as oleic acid are used in the preparation of injectable products. The injectable formulations can be sterilized, for example, by means of filtering through a bacteria-retaining filter, or by means of incorporating sterilizing agents in the form of sterile solid compositions which can be dissolved or dispersed in sterile water or another sterile injectable medium before use.

The compositions may comprise the ruthenium complex or the conjugate as a single agent or in combination with another therapeutic agent, such as an anti-tumor drug. In one embodiment, the pharmaceutical composition or the medicinal product of the invention comprises the combination of a ruthenium complex of formula (I) or a conjugate and an anti-tumor drug formulated for simultaneous, separate, or sequential administration. This means that the combination of the two compounds can be administered:

as a combination which is part of the same pharmaceutical formulation or medicinal product, administering the two compounds simultaneously; or as a combination of two dosage forms, each containing one of the substances, giving rise to the possibility of a simultaneous, sequential, or separate administration.

In a particular embodiment, the ruthenium complex of formula (I) or the conjugate and the anti-tumor drug are administered independently (i.e., in two dosage forms) but at the same time. In another particular embodiment, the ruthenium complex of formula (I) or the conjugate is administered first, and the other anti-tumor drug is then administered separately or sequentially. In an additional particular embodiment, the other anti-tumor drug is administered first and the compound of formula (I) or the conjugate is then administered separately or sequentially, as defined.

As it is used herein, the term "anti-cancer drug" or "anti-tumor drug," also referred to as "anti-cancer agent," "anti-tumor agent," or "antineoplastic agent," refers to an agent which is useful in the treatment of cancer. Anti-tumor agents according to the present invention include, without limitation, alkylating agents, antimetabolites, topoisomerase inhibitors, and anthracyclines.

As it is used herein, the term "alkylating agent" also referred to as "antineoplastic alkylating agent," refers to an agent mediating the transfer of an alkyl group from a molecule to DNA. The alkyl group can be transferred as an alkyl carbocation, a free radical, a carbanion, or a carbene (or the equivalent thereof). Alkylating agents are used in chemotherapy to cause damage to the DNA of cancer cells. Alkylating agents are generally divided into six classes:
  nitrogen mustards, such as chlormethine, cyclophosphamide, ifosfamide, melphalan, chlorambucil, etc.;
  ethyleneamine and methyleneamine derivatives, including altretamine, thiotepa, and the like;
  alkyl sulfonates, such as busulfan, etc.;
  nitrosoureas, such as carmustine, lomustine, etc.;
  triazenes, such as dacarbazine, procarbazine, temozolomide, etc.; and
  antineoplastic agents containing platinum, such as cisplatin, carboplatin, and oxaliplatin, which are commonly classified as alkylating agents, although they do not alkylate DNA, but rather cause the formation of covalent metallic adducts with the DNA through different means, etc.

As it is used herein, the term "antimetabolite" refers to a chemical which inhibits the use of a metabolite, which is another chemical that is part of normal metabolism. Such substances often have a structure similar to the structure of the metabolite with which they interfere, such as antifolates which interfere with the use of folic acid. The presence of antimetabolites may have toxic effects on cells, such as stopping cell growth and cell division, such that these compounds are used for cancer chemotherapy. The antimetabolites pose as a purine or a pyrimidine, preventing the incorporation thereof into DNA during the S phase (of the cell cycle), stopping normal development and division. They also affect RNA synthesis. However, given that thymidine is used in DNA but not in RNA (in which uracil is used instead), the inhibition of thymidine synthesis by thymidylate synthase selectively inhibits DNA synthesis with respect to RNA synthesis. The antimetabolites can be selected from:
  purine analogues, such as azathioprine, mercaptopurine, thioguanine, fludarabine, pentostatin, cladribine, etc.;
  pyrimidine analogues, such as 5-fluorouracil (5FU), floxuridine (FUDR), cytosine arabinoside (cytarabine), 6-azauracil (6-AU), etc.; or
  antifolates, such as methotrexate, pemetrexed, proguanil, pyrimethamine, trimethoprim, etc.

As it is used herein, term "topoisomerase inhibitor" refers to an agent designed for interfering with the action of topoisomerase enzymes (topoisomerases I and II). It is believed that topoisomerase inhibitors block the ligation step of the cell cycle, generating single- and double-stranded breaks which damage genome integrity. The introduction of these breaks subsequently leads to apoptosis and cell death. Non-limiting illustrative examples of topoisomerase inhibitors include etoposide, teniposide, topotecan, irinotecan, diflomotecan, or elomotecan.

As it is used herein, the term "anthracycline" refers to a class of (CCNS or cell cycle non-specific) drugs derived from Streptomyces bacteria strains and used in cancer chemotherapy. Non-limiting illustrative examples of anthracyclines include daunorubicin, doxorubicin, epirubicin, idarubicin, valrubicin, mitoxantrone, etc.

Other anti-cancer or anti-tumor agents according to the present invention include, without limitation, the following agents:
  angiogenesis inhibitors, such as angiostatin, endostatin, fumagillin, genistein, minocycline, and staurosporine;
  DNA synthesis inhibitors, such as aminopterin, ganciclovir, and hydroxyurea;
  enzyme inhibitors, such as S(+)-camptothecin, curcumin, 2-imino-1-imidazolidineacetic acid (cyclocreatine), hispidin, formestane, and mevinolin;
  microtubule inhibitors, such as colchicine and dolastatin 15; and
  other anti-tumor agents, such as 17-(allylamino)-17-demethoxygeldanamycin, apigenin, cimetidine, luteinizing hormone-releasing hormone, and pifithrin α.

Alternatively, the ruthenium complex and the anti-tumor drug can be bound to one another forming a conjugate. Therefore, in another aspect the invention relates to a conjugate comprising:
  a ruthenium complex of formula (I), and
  an anti-tumor drug.

Preferably, the ruthenium complex and the anti-tumor drug are covalently bound to one another directly or through a linker or spacer. Therefore, in a particular embodiment, the conjugate comprises a ruthenium complex of formula (I), an anti-tumor drug, and a linker.

Particular and preferred embodiments for the linker, the ruthenium complex, and the way of binding, are defined above in relation to the ruthenium complex-ABCG2 substrate conjugate.

Uses

One aspect of the invention is the use of a ruthenium complex or a conjugate as defined herein for preparing a medicinal product for treating cancer comprising cancer stem cells.

Another aspect of the invention relates to a ruthenium complex or a conjugate as defined herein for use thereof in the treatment of cancer comprising cancer stem cells.

Another aspect of the invention relates to a method for treating cancer comprising cancer stem cells, which method comprises administering to a patient in need of said treatment a therapeutically effective amount of a ruthenium complex or a conjugate as defined herein.

As they are used herein, the terms "treat," "treating," and "treatment" generally include the eradication, elimination, reversion, relief, modification, or control of cancer after its onset.

As it is used herein, the term "cancer," also referred to as "carcinoma," refers to a disease characterized by an uncontrolled proliferation of abnormal cells capable of invading adjacent tissues and spreading to distant organs. Within the context of the present invention, this term includes any type of cancer or tumor. Non-limiting illustrative examples of said cancers or tumors include blood cancers (e.g., leukemias or lymphomas), neurological tumors (e.g., astrocytomas or glioblastomas), melanoma, breast cancer, lung cancer, head and neck cancer, gastrointestinal tumors (e.g., stomach cancer, pancreatic cancer, or colorectal cancer (CRC)), liver cancer (e.g., hepatocellular carcinoma), renal cell cancer, genitourinary tumors (e.g., ovarian cancer, vaginal cancer, cervical cancer, bladder cancer, testicular cancer, prostate cancer), bone tumors, vascular tumors, etc.

As it is used herein, the term "cancer stem cell," also known as "CSC", refers to a type of stem cell which conserves self-renewal and differentiation capacities and is furthermore capable of causing tumors. Cancer stem cells are highly tumorigenic and chemoresistant. It is believed that these cells may be related to tumor relapse processes and/or metastasis after chemotherapy. The presence of cells of this type has been described in various types of tumors including, without limitation, hematologic neoplasm (Lapidot T et al. 1994 Nature 367(6464): 645-648), breast cancer (Al-Hajj M et al. 2003 Proc Natl Acad Sci USA 100 (7): 3983-3988), lung cancer (Kim C F et al. 2005 Cell 121(6): 823-835), colon cancer (O'Brien C A et al. 2007 Nature 445(7123): 106-110), prostate cancer (Collins A T et al. 2005 Cancer Res 65(23): 10946-10951), ovarian cancer (Szotec P P et al. 2006 Proc Natl Acad Sci USA 103(30): 11154-11159), and pancreatic cancer (Li C et al. 2007 Cancer Res 67(3): 1030-1037).

In a particular embodiment, the cancer comprising cancer stem cells is selected from hematologic neoplasm, breast cancer, lung cancer, colon cancer, prostate cancer, ovarian cancer, pancreatic cancer, cervical cancer, and kidney cancer. In an even more particular embodiment, the cancer is pancreatic cancer, preferably pancreatic adenocarcinoma.

As it is used herein, the term "hematologic neoplasm" refers to a heterogeneous group of cancers affecting the blood, the bone marrow, and lymph nodes. This term includes leukemias (affecting the bone marrow and spreading to peripheral blood) and lymphomas (originated in different lymphoid tissues: lymph nodes, spleen, and mucosa-associated lymphoid tissue). Hematologic neoplasms can be myeloid or lymphoid neoplasms depending on their origin.

Myeloid hematologic neoplasms include:
Chronic myeloproliferative neoplasms (MPNs): including chronic myeloid leukemia BCR-ABL positive, chronic neutrophilic leukemia, polycythemia vera, primary myelofibrosis, essential thrombocytopenia, chronic eosinophilic leukemia, systemic mastocytosis, and unclassifiable myeloproliferative neoplasms.
Myeloid and lymphoid neoplasms with eosinophilia and PDGFRA, PDGFRB, or FGFR1 anomalies.
Myelodysplastic syndromes (MDS): including refractory cytopenia with single lineage dysplasia, sideroblastic refractory anemia, refractory cytopenia with multilineage dysplasia, refractory anemia with excess blasts, myelodysplastic syndrome with isolated del(5q), unclassifiable myelodysplastic syndrome, and pediatric myelodysplastic syndrome.
Myelodysplastic/myeloproliferative neoplasms (MDS/MPN): include chronic myelomonocytic leukemia, atypical chronic myeloid leukemia BCR-ABL negative, juvenile myelomonocytic leukemia, and unclassifiable myelodysplastic/myeloproliferative neoplasm.
Acute myeloid leukemias (AMLs): including AMLs with recurrent genetic alterations, AMLs with t(8;21) (q22; q22) RUNX1, AMLs with myelodysplasia-related changes, therapy-related AMLs, AML without characteristics typical of the preceding categories, myeloid sarcoma, Down syndrome-related myeloid proliferations, and blastic plasmacytoid dendritic cell neoplasm.
Acute leukemias of ambiguous lineage.
Lymphoid hematologic neoplasms include:
Lymphoid neoplasms of precursor cells: including B-cell lymphoblastic lymphoma/leukemia and T-cell lymphoblastic lymphoma/leukemia.
Mature B-cell neoplasms.
Mature T-cell and NJ cell neoplasms.
Hodgkin's lymphoma.

As it is used herein, the term "breast cancer," also known as "malignant breast neoplasm" or "breast tumor," refers to cancer originated in the breast tissue, usually in the inner lining of milk ducts or lobules that supply milk to the ducts. Depending on the receptor state detected by means of immunohistochemistry, particularly on the presence or absence of estrogen receptor (ER), progesterone receptor (PR), and on the expression level of HER2/neu (normal expression/underexpression with respect to overexpression), breast cancers can be divided into ER-positive (ER+) breast cancer, ER-negative (ER−) breast cancer, PR-positive (PR+) breast cancer, PR-negative (PR−) breast cancer, HER2-positive (HER2+) breast cancer (cancer overexpressing HER2), HER2-negative (HER2−) breast cancer (cancer expressing normal levels of HER2, or underexpressing HER2, or not expressing a detectable level of HER2), hormone receptor-negative breast cancer, i.e., breast cancer without estrogen or progesterone receptors (abbreviated as ER−/PR− breast cancer); and triple negative breast cancer, i.e., breast cancer without estrogen or progesterone receptors and with normal expression/underexpression (or with the absence of a detectable expression level) of HER2 (abbreviated as ER−/PR−/HER2-breast cancer).

As it is used herein, the term "lung cancer," also referred to as "pulmonary cancer" or "pulmonary tumor," refers to any uncontrolled cell growth in lung tissues, including, but not limited to, microcytic lung carcinoma, combined microcytic carcinoma, non-microcytic lung carcinoma, sarcomatoid carcinoma, salivary gland tumor, carcinoid tumor, adenosquamous carcinoma, pleuropulmonary blastoma, and carcinoid tumor.

As it is used herein, the term "prostate cancer" refers to an uncontrolled (malignant) growth of cells originating from the prostate gland.

As it is used herein, the term "ovarian cancer," also referred to as "ovarian tumor," refers to a group of tumors originating in the ovaries and includes, without limitation, serous ovarian cancer, non-invasive ovarian cancer, mixed phenotype ovarian cancer, mucinous ovarian cancer, endometrioid ovarian cancer, ovarian clear cell cancer, ovarian serous papillary cancer, Brenner tumor of ovary, and undifferentiated adenocarcinoma.

As it is used herein, the term "pancreatic cancer," also referred to as "pancreatic tumor," refers to cancer derived from pancreatic cells including, but not limited to, adenocarcinomas, adenosquamous carcinomas, signet ring cell carcinomas, hepatoid carcinomas, colloid carcinomas, undifferentiated carcinomas, undifferentiated carcinomas with osteoclast-like giant cells, and islet cell carcinomas.

As it is used herein, the term "cervical cancer," also referred to as "cervical carcinoma," refers to a malignant tumor developed in the lower fibromuscular portion of the uterus which projects into the vagina.

As it is used herein, the term "kidney cancer," also referred to as "renal cancer," "renal adenocarcinoma," or "renal cell cancer," refers to any malignant proliferative disorder of kidney cells, particularly to a cancer formed by malignant cells in the tubules of the kidney.

In a particular embodiment, cancer stem cells have low c-MYC expression levels.

As it is used herein, the term "c-MYC" refers to the gene encoding a multifunctional nuclear phosphoprotein which participates in cell cycle progression, apoptosis, and cell transformation. The c-MYC protein in humans has the sequence shown with accession number P01106 in the Uniprot database dated 2 Nov. 2016.

As it is used herein, the term "expression level" of a gene refers to the amount of the gene product that can be measured in cells, in which the gene product can be a transcription product or a translation product. Accordingly, the expression level may correspond to a nucleic acid product of the gene such as an mRNA or a cDNA or a polypeptide product of the gene.

As understood by one skilled in the art, the expression level of the c-MYC gene can be quantified by means of quantifying the expression levels of the protein encoded by said gene, i.e., c-MYC, or by means of determining the activity of said protein. c-MYC activity can be determined using various assays known by one skilled in the art, by way of non-limiting illustrative example, by determining transcriptional activity.

The expression level of the protein can be quantified by means of any conventional method which allows detecting and quantifying said protein in cells, such as Western blot Western, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks.

Moreover, the quantification of the expression levels of a gene can be determined by measuring the levels of the RNA resulting from the transcription of said gene (messenger RNA or mRNA), or alternatively, from the complementary DNA (cDNA) of said gene. Virtually any conventional method can be used within the framework of the invention for detecting and quantifying the levels of mRNA or its corresponding cDNA. By way of non-limiting illustration, the mRNA levels encoded by said gene can be quantified by means of using conventional methods, for example, methods which comprise amplifying the mRNA and quantifying the amplification product of said mRNA, such as electrophoresis and staining, or alternatively, by means of Southern blot and the use of suitable probes, Northern blot and the use of probes specific for the mRNA of the gene of interest or its corresponding cDNA, nuclease S1 mapping, RT-LCR, hybridization, microarrays, RT-PCR, etc.

As it is used herein, "low expression levels" refers to the expression level of a gene that is lower than the reference value. In particular, cells can be considered to have low c-MYC expression levels when the expression levels in the cells are at least 1.1 times, 1.5 times, 5 times, 10 times, 20 times, 30 times, 40 times, 50 times, 60 times, 70 times, 80 times, 90 times, or 100 times lower, or even lower, with respect to the reference value.

As it is used herein, "reference value" refers to a value obtained in the laboratory and used as a reference for the expression values of c-MYC. The reference value or reference level can be an absolute value, a relative value, a value a value having an upper and/or lower limit, a range of values, an average value, a median value, a mean value, or a value as compared to a specific control or reference value. The reference value can be based on an individual sample value, such as a value obtained from a cancer stem cell sample of a subject, for example. The reference value can be based on a large number of samples, such as the expression values of c-MYC in cancer stem cell samples of a population of subjects. In a particular embodiment, the reference value corresponds to the expression level in a cancer not having cancer stem cells.

The inventors have observed that the metallation reaction increases upon irradiating with light. Therefore, in a preferred embodiment the ruthenium complexes or the conjugates of the invention are used in the treatment of cancer in the presence of irradiation with light. In one embodiment, the irradiation is performed with ultraviolet (UV), visible, or near infrared (IR) light. In a particular embodiment, irradiation is performed with light having a wavelength between 200 and 1000 nm, preferably between 300 and 800 nm, more preferably between 400 and 600 nm. Preferably, irradiation is performed with light having a wavelength between 400 and 500 nm.

Therefore, in one embodiment the invention relates to a ruthenium complex or a conjugate as defined herein for use thereof in the treatment of cancer comprising cancer stem cells by means of irradiation with light, preferably with light having a wavelength between 200 and 1000 nm, more preferably between 300 and 800 nm, more preferably between 400 and 600 nm. In a particular embodiment, irradiation is performed with light having a wavelength between 400 and 500 nm.

Another aspect of the invention relates to a method for treating cancer comprising cancer stem cells, which method comprises administering to a patient in need of said treatment a therapeutically effective amount of a ruthenium complex or a conjugate as defined herein, and where said method comprises irradiating said ruthenium complex or conjugate with light, preferably with light having a wavelength between 200 and 1000 nm, more preferably between 300 and 800 nm, more preferably between 400 and 600 nm. In a particular embodiment, irradiation is performed with light having a wavelength of between 400 and 500 nm.

Methods suitable for performing irradiation at the desired wavelength are known by one skilled in the art.

Additionally, it has been observed that the ruthenium complexes of formula (I) and the corresponding conjugates, wherein X is selected from $SR_1R_2$ are kinematically stable and only react with c-MYC by means of irradiation with light. Therefore, in these cases it is possible to provide an inactive derivative that can be handled with ease and activated in a controlled manner at the desired actuation time and place by means of irradiation with light. This represents a significant advantage in cancer treatment. Therefore, a preferred embodiment of the invention relates to the ruthenium complexes as defined herein, wherein X is selected from $SR_1R_2$.

The following non-limiting examples seek to illustrate the present invention and must not be interpreted as limiting the scope thereof.

EXAMPLES

High-performance liquid chromatography (HPLC) was carried out using Agilent 1100 liquid chromatography-mass spectrometer equipment. Analytical HPLC was carried out using a Phenomenex Luna-C18 reversed-phase analytical column (10×250 mm, 5 μm), 1 mL/min, with different gradients (see below). The adducts were purified in a Phenomenex Luna-C18 reversed-phase analytical column (250× 10 mm). Electrospray ionization mass spectrometry (ESI/MS) was performed with an Agilent 1100 Series LC/MSD VL G1956A model in positive polarity mode.

Mobile Phases:

a) A: $H_2O$ containing 0.1% TFA, B: ACN containing 0.1% TFA.

Gradient 1: 0%→50% of B for 40 min.

b) A: 95:5 $H_2O$:ACN containing 100 mM TEAA, B: 70:30 ACN:$H_2O$ containing 100 mM TEAA.

Gradient 2: 0% of B for 5 min followed by 0%→100% of B for 55 min.

Gradient 3: 10%→50% of B for 40 min.

Example 1. Synthesis of Ruthenium(II) Complexes

Example 1A. Synthesis of Complex 1

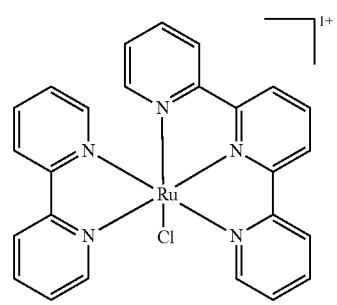

Ruthenium complex 1 was prepared following the method described in Kaveevivitchai et al., Inorg. Chem. 2012, 51, 2930. $RuCl_3 \cdot 3H_2O$ (500 mg, 2 mmol) and 2,2':6',2''-terpyridine (460 mg, 1 equiv) was dissolved in a deoxygenated $H_2O$:EtOH 1:1 mixture (20 mL), and heated at reflux for 4 h in the dark. The resulting precipitate was washed with EtOH (×3) and $Et_2O$ and used directly in a second step involving treatment with 2,2'-bipyridine (312 mg, 1 equiv) in a deoxygenated $H_2O$:EtOH 1:1 mixture (20 mL) and heated at reflux overnight. Precipitation with excess $KPF_6$ gave rise to the salt [Ru(terpy)(bpy)Cl]$PF_6$ 1 as a brown powder with an overall yield of 60% (800 mg). EM-ESI$^+$ (m/z): Calculated for $C_{25}H_{19}ClN_5Ru$: 525.0. Found: 526.0 [M+1H]$^+$.

Example 1B. Synthesis of Complex 2

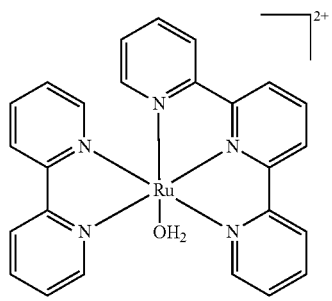

Ruthenium complex 2 was prepared following a modified method of the literature (Takeuchi et al., Inorg. Chem. 1984, 23, 1845). Complex 1 (150 mg, 0.22 mmol) was dissolved in a deoxygenated $H_2O$:EtOH 1:1 mixture (20 mL) and heated at reflux for 1 h. The crude was concentrated, and the product was purified by means of reversed-phase HPLC (HPLC-FR), 4 mL/min, gradient of 5 to 95% of B for 35 min (A: $H_2O$ containing 0.1% TFA, B: ACN with 0.1% TFA), and identified as the desired product by means of mass spectrometry (78% yield). EM-ESI$^+$ (m/z): Calculated for $C_{25}H_{21}N_5ORu$: 509.1. Found: 508.0 [M−1H]$^+$.

Example 1C. Synthesis of Complex 4

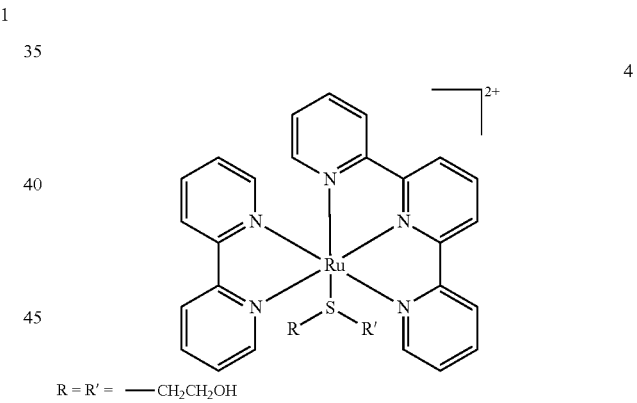

Ruthenium complex 4 was prepared following a modified method of the literature (Bahreman et al., Eur. J. 2012, 18, 10271). Complex 1 (50 mg, 0.07 mmol) was dissolved in thiodiethanol (10 μL, 1.3 equiv) and heated at reflux overnight in the dark. The product was purified by means of HPLC-FR at 4 mL/min with a gradient of 5 to 95% of B for 35 min (A: $H_2O$ containing 0.1% TFA, B: ACN containing 0.1% TFA) and identified as the desired product by means of mass spectrometry and NMR (33 mg, 65% yield). $^1$H NMR (500 MHz, $D_2O$) 9.70 (m, 1H), 8.55 (m, 3H), 8.38 (m, 2H), 8.31 (m, 1H), 8.23 (m, 2H), 7.90 (m, 3H), 7.72 (m, 3H), 7.24 (ddd, J=7.6, 5.6, 1.3 Hz, 2H), 7.13 (dt, J=4.1, 2.0 Hz, 1H), 6.98 (ddd, J=7.2, 4.8, 1.3 Hz, 1H), 3.20 (t, J=5.9 Hz, 4H), 1.87 (m, 4H). 13C NMR (500 MHz, $D_2O$) δ 157.68 (C), 157.15 (C), 156.62 (C), 152.96 (CH), 151.72 (CH), 149.42 (CH), 138.62 (CH), 138.02 (CH), 137.56 (CH), 136.56 (CH), 128.01 (CH), 127.29 (CH), 126.52 (CH), 124.63 (C), 124.25

(CH), 123.77 (CH), 123.37 (CH), 57.57 (CH$_2$), 35.01 (CH$_2$). EM-ESI$^+$ (m/z): Calculated for C$_{29}$H$_{29}$N$_5$O$_2$RuS: 613.1. Found: 612.0 [M−1H]$^+$.

Example 1D. Synthesis of Complex 5

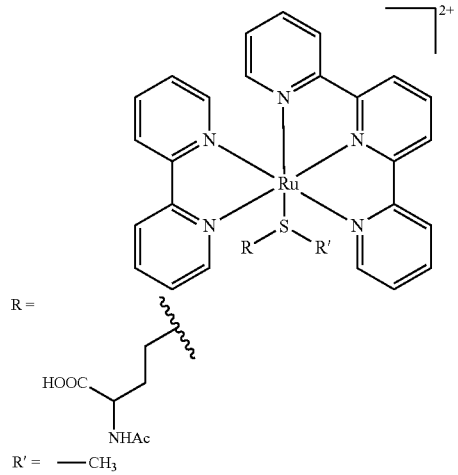

Ruthenium complex 5 was prepared following a modified method of the literature (Goldbach et al., Chem. Eur. J. 2011, 17, 9924). Complex 1 (50 mg, 0.07 mmol) and N-acetyl-L-methionine (19 mg, 5 equiv) were dissolved in a deoxygenated H$_2$O:EtOH 1:1 mixture (2 mL) and heated at reflux overnight in the dark. The product was purified by means of HPLC-FR at 4 mL/min with a gradient of 5 to 95% of B for 35 min (A: H$_2$O containing 0.1% TFA, B: ACN containing 0.1% TFA) and identified as the desired product by means of mass spectrometry (24 mg, 45% yield). EM-ESI$^+$ (m/z): Calculated for C$_{32}$H$_{32}$N$_6$O$_3$RuS: 682.1. Found: 681.0 [M−1H]$^+$.

Example 1E. Synthesis of the Ruthenium Complex-Riboflavin 10 Conjugate

This synthesis requires mixing aquo complex 2 and 1 thioether ligand equivalent in water at 80° C. in the dark. The course of the reaction can be monitored using RP-HPLC. After purification by means of RP-HPLC, compound [10].TFA$_2$ was obtained as a brown powder.

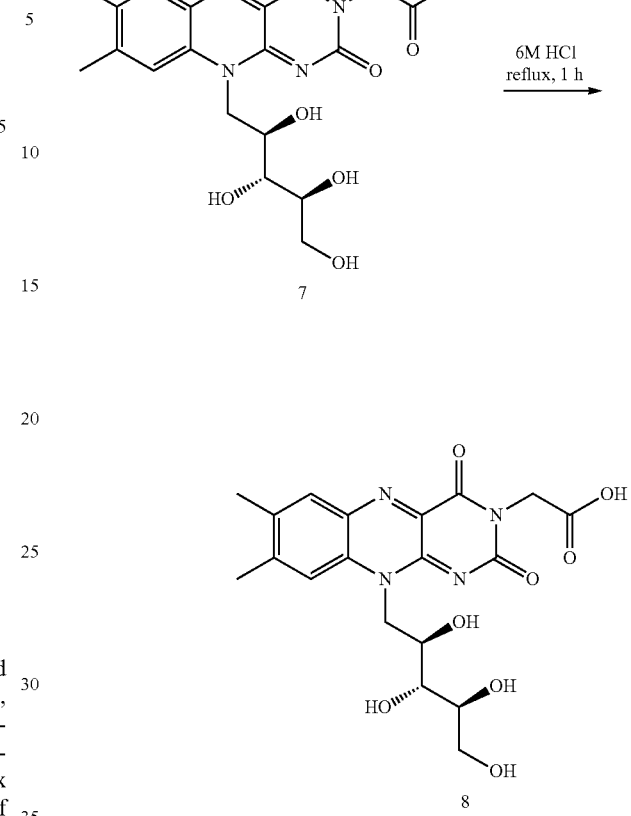

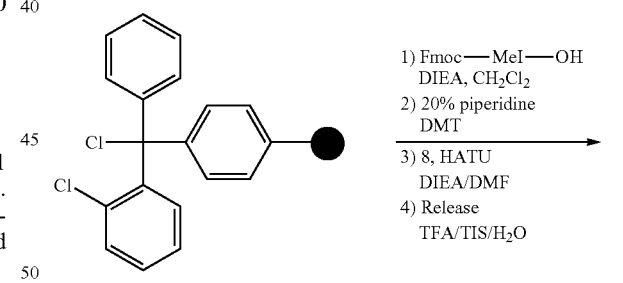

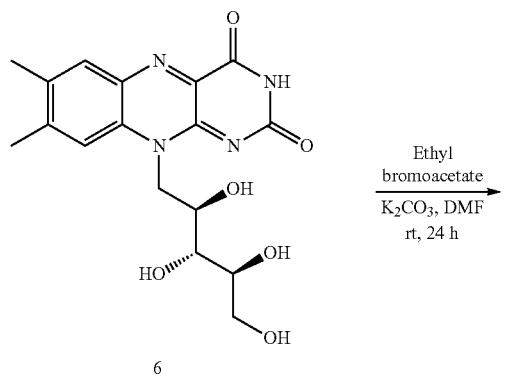

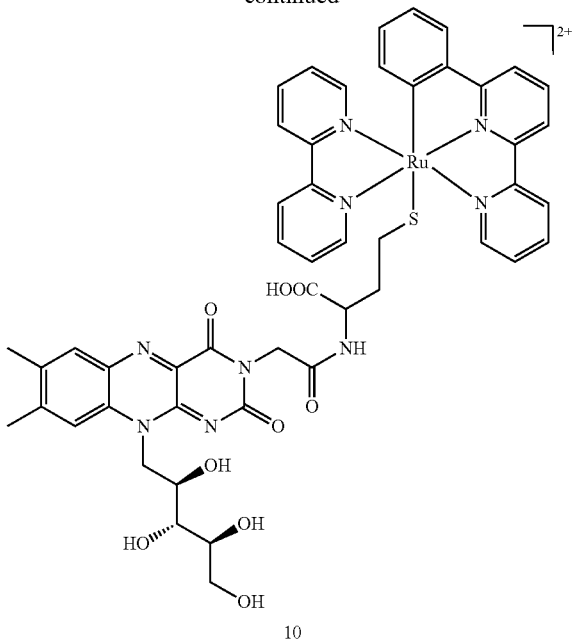

10

Compound 7. A suspension of riboflavin 6 (2 g, 5.3 mmol, 1.0 equiv), potassium carbonate (1.5 equiv, 8 mmol, 1.1 g), in 12 mL of dry DMF at room temperature was stirred for 45 min under inert atmosphere. An ethyl bromoacetate solution (2 equiv, 10.6 mmol, 1.1 mL) in 4 mL of dry DMF was then added dropwise and stirring was maintained until the reaction (24 h) was completed. The solvent was evaporated and the resulting residue was purified by means of column chromatography (10% MeOH/$CH_2Cl_2$) to obtain 7 as a yellow solid (1.2 g, 50%). $^1$H NMR (500 MHz, $DC_3OD$) δ 8.08 (s, 1H), 4.82 (s, 2H), 4.47 (i, 1H), 4.26 (q, J=6.8 Hz, 2H), 3.85 (m, 4H), 3.69 (dd, J=11.4, 6.0 Hz, 2H), 2.60 (s, 3H), 2.49 (s, 3H), 1.31 (t, J=6.8 Hz, 3H). EMAR (ESI): Calculated for $CH_6N_4O_8$: 462.18. Found: 463.2 [M+1H]$^+$.

Compound 8. Compound 7 (400 mg, 0.86 mmol) was suspended in 6 M HCl (15 mL) and heated at reflux for 1 h. The reaction was neutralized with NaOH until about pH 7, diluted with water, and purified by means of preparative RP-Büchi Sepacore (gradient: 5% of B, 5 min; 15%→95% of B, 40 min). The solvent was eliminated at reduced pressure, giving rise to a yellow solid (260 mg, 69%). $^1$H NMR (500 MHz, $D_2O$) δ 7.71 (s, 1H), 7.64 (s, 1H), 4.87 (m, 1H), 4.59 (s, 2H), 4.23 (m, 1H), 3.78 (m, 4H), 3.60 (m, 1H), 2.40 (s, 3H), 2.28 (s, 3H). EMAR (ESI): Calculated for $C_{19}H_{22}N_4O_8$: 434.14. Found: 435.2 [M+1H]$^+$, 457.1 [M+1Na]$^+$.

Compound 9. A mixture of Fmoc-Met-OH (371 mg, 1 mmol) and DIEA (695 μL, 4 mmol, 4 equiv) was added to a suspension of 2-chlorotrityl resin (0.25 mmol) in 2.5 mL of $CH_2Cl_2$, and the mixture was stirred for 50 min. The resin was washed with $CH_2Cl_2$/MeOH/DIEA (17:2:1) (3×5 mL, 2 min), $CH_2Cl_2$ (3×5 mL, 2 min), and treated with 20% piperidine in DMF (1×5 mL, 10 min).

A solution of compound 8 (170 mg, 0.4 mmol), DIEA/DMF 0.2 M (8.2 mL, 1.6 mmol, 4 equiv), and HATU (152 mg, 0.4 mmol, 1 equiv) was added to the preceding resin (0.4 mmol) and the suspension was stirred for 50 min. The resin was washed with DMF (3×10 mL, 2 min) and $CH_2Cl_2$ (2×10 mL, 2 min) and then treated with the deprotection cocktail (900 μL TFA, 50 μL $CH_2Cl_2$, 25 μL $H_2O$ and 25 μL TIS; 1 mL of cocktail/40 mg resin) for 1.5-2 h. After filtration, the crude was concentrated at reduced pressure.

The residue obtained after the concentration was purified by means of preparative RP-Büchi Sepacore, gradient: 5% of B, 5 min; 15%-95% of B, 40 min (A: $H_2O$ containing 0.1% TFA, B: MeOH containing 0.1% TFA). The suitable fractions were collected, concentrated, and lyophilized to obtain the desired product 9 as a pale yellow powder (50 mg, 23%). $^1$H NMR (500 MHz, $D_2O$) δ 8.00 (s, 1H), 7.97 (s, 1H), 5.13 (m, 1H), 4.97 (d, J=14.0 Hz, 1H), 4.86 (m, 2H), 4.46 (m, 1H), 3.97 (m, 2H), 3.89 (d, J=11.9 Hz, 1H), 3.75 (m, 1H), 3.01 (m, 2H), 2.76 (d, J=2.4 Hz, 1H), 2.61 (s, 3H), 2.50 (s, 3H), 2.26 (m, 2H), 2.09 (s, 3H). EMAR (ESI): Calculated for $C_{24}H_{31}N_5O_9S$: 565.18. Found: 566.19.

Compound 10. Complex 2 (35 mg, 0.07 mmol) and compound 9 (40 mg, 1 equiv) were dissolved in deoxygenated $H_2O$:EtOH 1:1 (2 mL) and heated at reflux overnight in the dark. The product was purified by means of RP-HPLC at 4 mL/min with a gradient of 5 to 95% of B for 35 min (A: $H_2O$ containing 0.1% TFA, B: ACN containing 0.1% TFA). Suitable fractions were collected, concentrated and lyophilized to obtain the desired product 10 as a brown powder (10 mg, 13%). $^1$H NMR (500 MHz, $D_2O$) δ 8.64 (dd, J=19.0, 8.2 Hz, 2H), 8.48 (dd, J=24.0, 8.1 Hz, 2H), 8.32 (m, 2H), 8.09 (m, 3H), 7.98 (m, 2H), 7.81 (m, 3H), 7.62 (t, J=5.4 Hz, 1H), 7.54 (m, 3H), 7.26 (m, 2H), 7.09 (t, J=6 Hz, 1H), 5.15 (m, 1H), 4.91 (m, 2H), 4.60 (m, 1H), 4.50 (m, 2H), 3.97 (m, 2H), 3.86 (m, 1H), 3.73 (dd, J=11.8, 5.8 Hz, 1H), 2.60 (s, 3H), 2.36 (s, 3H), 1.92 (m, 1H), 1.79 (m, 2H), 1.69 (m, 1H), 1.24 (s, 3H). EMAR (ESI): Calculated for $C_{49}H_{50}N_{10}O_9RuS$: 1056.25. Found: 1055.25 [M−1H]$^+$.

Example 2. GMP and c-MYC Binding Assays

General Method of the Assays for Metallating DNAs Using Irradiation

The oligonucleotides (10 μM) were treated with ruthenium complexes in 10 mM potassium phosphate buffer with 100 mM KCl, pH=7.5, for 30 min at room temperature. The solutions were incubated in the dark or irradiated with a high-power LED. For irradiation, the samples were placed in a standard 10 mm cuvette in a sample support and irradiated with a high-power LED unit at 455 nm with 900 mW for 30 min (Thorlabs, Inc., Catalog No.: M455L3). The light of the LED is collimated by a planar-convex lens with a short focal length for the purpose of maximizing irradiation power.

Example 2A. Complex 1-GMP Binding Assays

First, guanosine monophosphate (GMP) metallating capacity of complex 1 was studied. To that end, complex 1 (250 μM) was mixed with 3 equivalents of GMP (750 μM) in 10 mM phosphate buffer (pH=7.5) and 100 mM NaCl. After 30 min at room temperature, partial formation (more than 50%) of the aquo [Ru(terpy) (bpy)$H_2O$]$^{2+}$ complex (2) was observed, whereas the GMP remained essentially unreacted (FIG. 1, line b). The subsequent 2-hr sample incubation gave rise to metallated product 3 and to aquo complex 2, with the starting chlorine complex being completely consumed (FIG. 1, line d). Irradiation of the sample for 30 min (λ=455 nm) gave rise to the exclusive formation of monoadduct 3 (conversion of about 80% based on the disappearance of GMP, FIG. 1, line c).

Figure 2:
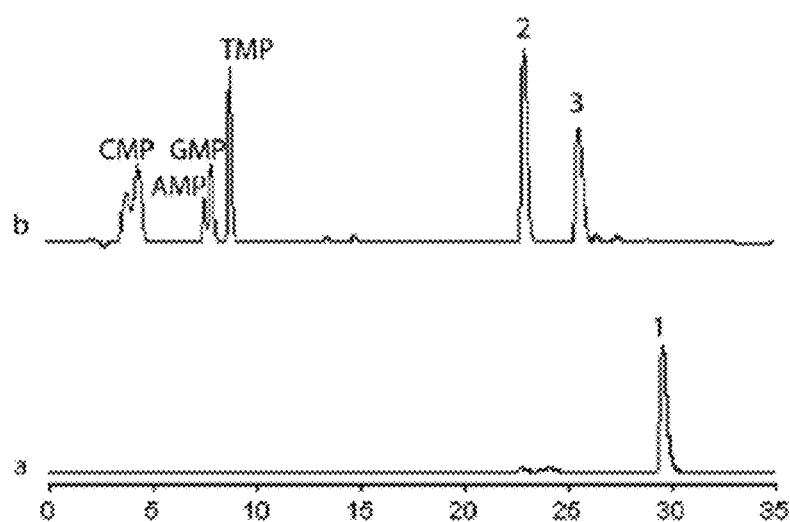
FIG. 2. HPLC chromatograms for the reaction of complex 1 (250 μM) with GMP (3 equiv, 750 μM), AMP (3 equiv, 750 μM), TMP (3 equiv, 750 μM), and CMP (3 equiv, 750 μM) in 10 mM phosphate buffer (pH=7.5) and 100 mM NaCl: (a) complex 1; (b) mixture after 30 min of irradiation at 455 nm. Eluent: ACN/H$_2$O gradient 1, 0.1% TFA. $\lambda_{obs}$=222.

To confirm that GMP metallation is completely orthogonal, competitive experiments were carried out with the other three nucleotides (AMP, CMP, and TMP). Specifically, complex 1 (250 μM) was mixed with GMP (3 equiv, 750

µM), AMP (3 equiv, 750 µM), TMP (3 equiv, 750 µM), and CMP (3 equiv, 750 µM) in 10 mM phosphate buffer (pH=7.5) and 100 mM NaCl. After irradiating at 455 nm for 30 min, the formation of the aquo $[Ru(terpy)(bpy)H_2O]^2$ complex (2) and the exclusive modification of the GMP was observed, giving rise to monoadduct 3 (FIG. 2).

Figure 3:
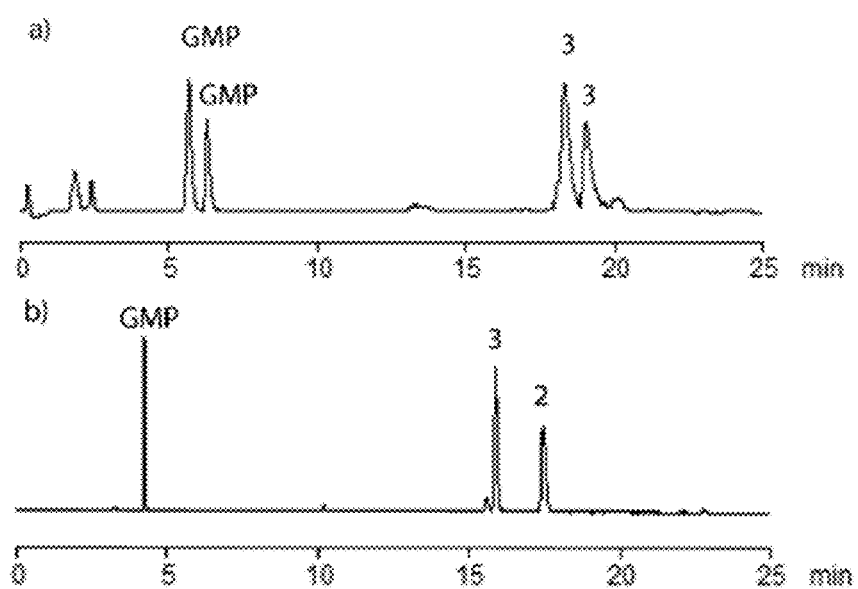
FIG. 3. a) HPLC chromatogram for the reaction of complex 1 (250 μM) and GMP (3 equiv, 750 μM) in the presence of H-Lys(Boc)-OH (3 equiv, 750 μM) in 10 mM phosphate buffer (pH=7.5) and 100 mM NaCl: complex 1, GMP, and H-Lys(Boc)-OH after 30 min of irradiation at 455 nm. Eluent: ACN/H$_2$O gradient 1, in the presence of TFA. $\lambda_{obs}$=222. GMP appears as two peaks because it is a mixture of isomers 2'- and 3'-monophosphate. b) HPLC chromatogram for the reaction of complex 1 (250 μM) and GMP (3 equiv, 750 μM) in the presence of Ac-Cys-OH (3 equiv, 750 μM) in 10 mM phosphate buffer (pH=7.5) and 100 mM NaCl: complex 1, GMP, and Ac-Cys-OH after 30 min of irradiation at 455 nm. Eluent: ACN/H$_2$O gradient 1, in the presence of TFA. $\lambda_{obs}$=222.

The selectivity of GMP metallation in the presence of lysine and cysteine derivatives was also confirmed. To that end, complex 1 (250 µM) was mixed with GMP (3 equiv, 750 µM) in the presence of H-Lys(Boc)-OH (3 equiv, 750 µM) or Ac-Cys-OH (3 equiv, 750 µM) in 10 mM phosphate buffer (pH=7.5) and 100 mM NaCl. After irradiating at 455 nm for 30 min, the exclusive modification of the GMP was observed, giving rise to monoadduct 3 (FIG. 3).

Example 2B. Complex 1-c-MYC Binding Assays

Figure 4:
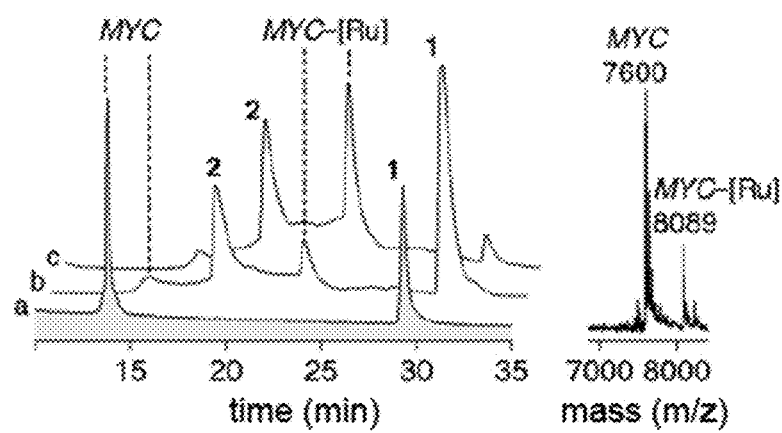
FIG. 4. (Left) HPLC of a mixture of c-MYC (10 μM) and complex 1 (5 equiv) in 10 mM phosphate buffer (pH=7.5) and 100 mM KCl at room temperature: a) in the dark at t=0; (b) after 30 min in the dark; (c) initial mixture after 30 min of irradiation at 455 nm, Eluent: ACN/H$_2$O gradient 3, in the presence of TEAA. $\lambda_{obs}$=260 nm. (Right) Mass spectrum of the metallated product (MYC-[Ru]) showing peaks corresponding to the complex (m/z=8089) and the demetallated fragment (m/z=7600).

A 10 µM solution of parallel c-MYC quadruplex d[TTGAG$_3$TG$_3$TAG$_3$TG$_3$TA$_3$] (SEQ ID NO: 1) was treated with 5 equivalents of ruthenium complex 1 in 10 mM phosphate buffer (pH=7.5) and 100 mM KCl and the mixture was irradiated for 30 min ($\lambda$=455 nm) at room temperature. The formation of a product with mass corresponding to the monoadduct derivative MYC-[Ru] with a conversion of 81% was observed (FIG. 4, line c). Reaction in the absence of light, with a conversion of about 41% after 30 min at room temperature was also observed (FIG. 4, line b).

Example 2C. Complex 4-GM Binding Assays

Figure 5:
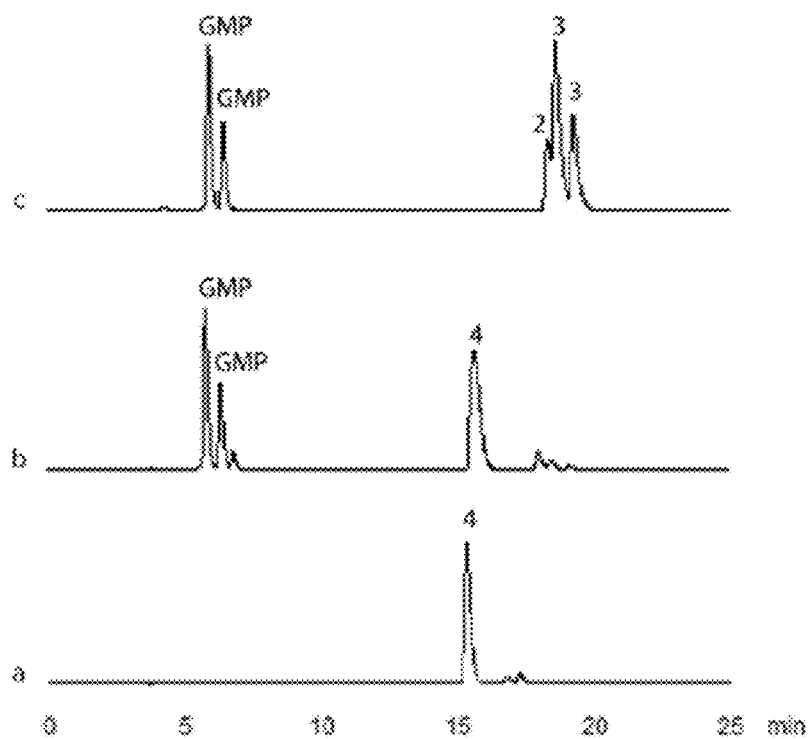
FIG. 5. HPLC chromatograms for the reaction of complex 4 (250 μM) and GMP (750 μM) in 10 mM phosphate buffer (pH=7.5) and 100 mM NaCl: (a) complex 4; (b) after 30 min in the dark; (c) the same mixture after 30 min of irradiation at 455 nm. Eluent: ACN/H$_2$O gradient 1, in the presence of TFA. $\lambda_{obs}$=222 nm.

Complex 4 (250 µM) was mixed with 3 equivalents of GMP (750 µM) in 10 mM phosphate buffer (pH=7.5) and 100 mM NaCl. After 30 min at room temperature in the dark, no new product formation was observed (FIG. 5, line b). However, when the initial sample was irradiated for 30 min ($\lambda$=455 nm), the exclusive formation of monoadduct 3 was observed (FIG. 5, line c).

Example 2D. Complex 4-c-MYC Binding Assays

Figure 6:
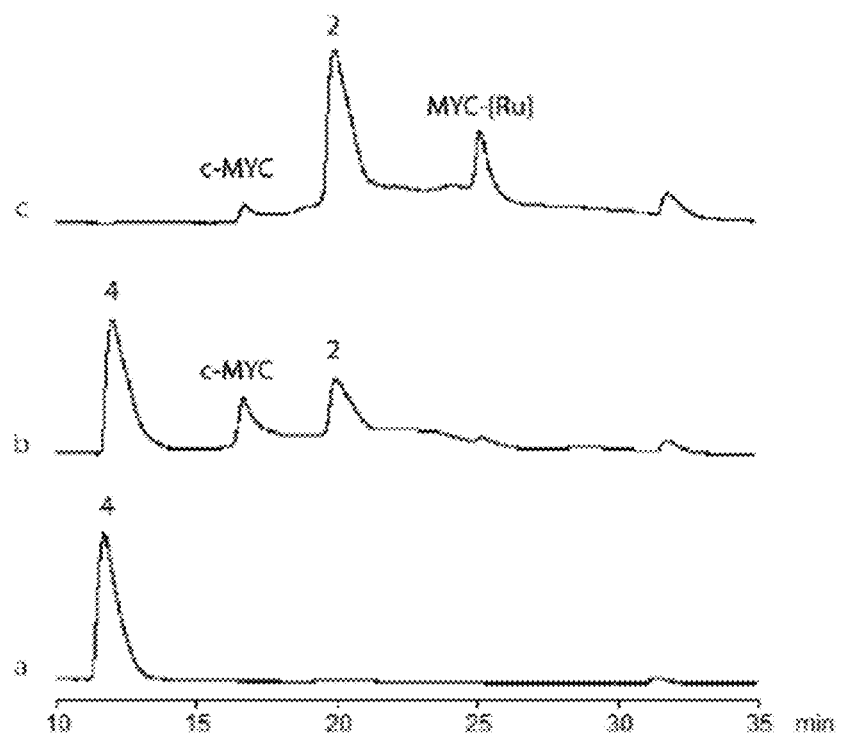
FIG. 6. HPLC of a mixture of c-MYC (10 μM) and complex 4 (5 equiv) in 10 mM phosphate buffer (pH=7.5) and 100 mM KCl at room temperature: (a) complex 4; (b) after 30 min in the dark; (c) the same mixture after 30 min of irradiation at 455 nm. Eluent: ACN/H$_2$O gradient 3, in the presence of TEAA. $\lambda_{obs}$=260 nm.

A 10 µM solution of quadruplex c-MYC was treated with 5 equivalents of ruthenium complex 4 in 10 mM phosphate buffer (pH=7.5) and 100 mM KCl. The irradiation of the mixture for 30 min ($\lambda$=455 nm) at room temperature gave rise to the formation of the product MYC-[Ru] (FIG. 6, line c). When the reaction was carried out in the dark, formation of metallated product was not observed after 30 min (FIG. 6, line b).

Example 2E. Complex 5-GMP Binding Assays

Figure 7:
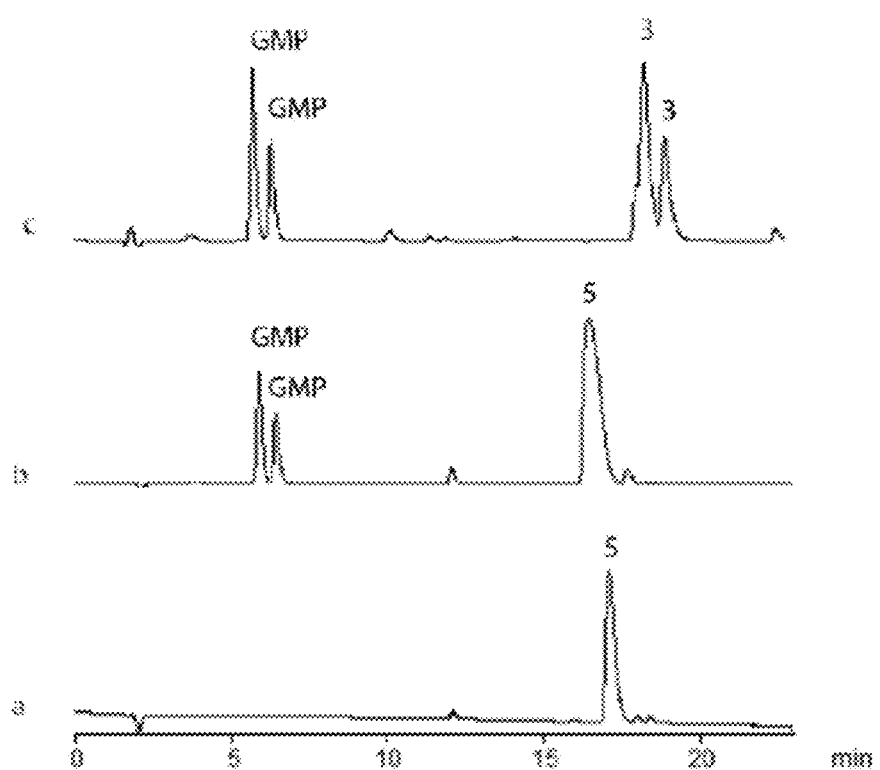
FIG. 7. HPLC chromatograms for the reaction of complex 5 (250 μM) and GMP (750 μM) in 10 mM phosphate buffer (pH=7.5) and 100 mM NaCl: (a) complex 5; (b) after 30 min in the dark; (c) the same mixture after 30 min of irradiation at 455 nm. Eluent: ACN/H$_2$O gradient 1, in the presence of TFA. $\lambda_{obs}$=260 nm.

Complex 5 (250 µM) was mixed with 3 equivalents of GMP (750 µM) in 10 mM phosphate buffer (pH=7.5) and 100 mM NaCl. After 30 min at room temperature in the dark, no new product formation was observed (FIG. 7, line b). However, when the initial sample was irradiated for 30 min ($\lambda$=455 nm), the exclusive formation of monoadduct 3 was observed (FIG. 7, line c).

Example 2F. Complex 5-c-MYC Binding Assays

Figure 8:
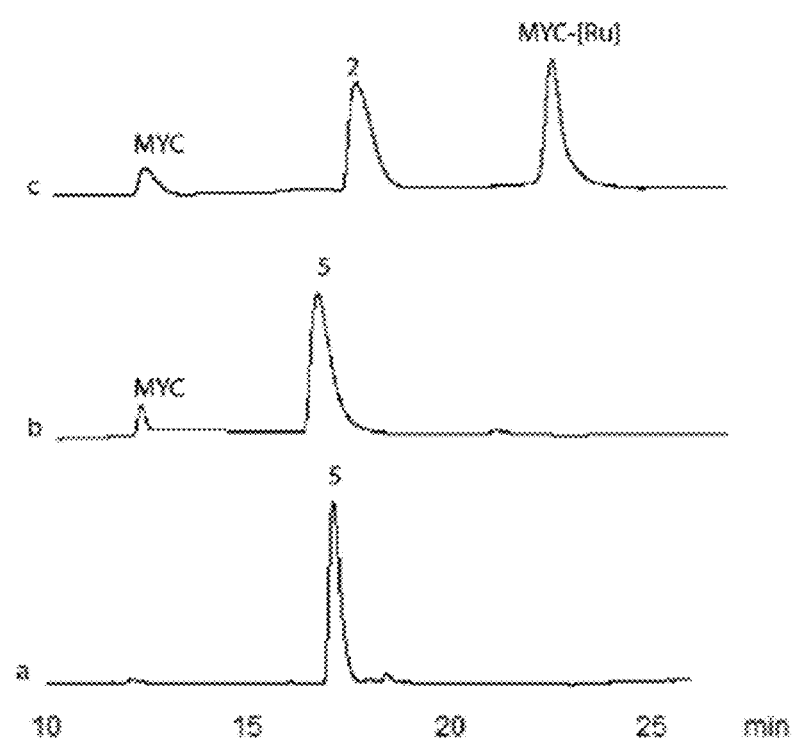
FIG. 8. HPLC of a mixture of c-MYC (10 μM) and complex 5 (5 equiv) in 10 mM phosphate buffer (pH=7.5) and 100 mM KCl at room temperature: (a) complex 5; (b) after 30 min in the dark; (c) the same mixture after 30 min of irradiation at 455 nm. Eluent: ACN/H$_2$O gradient 3, in the presence of TEAA. $\lambda_{obs}$=260 nm.

A 10 µM solution of quadruplex c-MYC was treated with 5 equivalents of ruthenium complex 5 in 10 mM phosphate buffer (pH=7.5) and 100 mM KCl. The irradiation of the mixture for 30 min ($\lambda$=455 nm) at room temperature gave rise to the formation of the product MYC-[Ru] (FIG. 8, line c). When the reaction was carried out in the dark, the formation of metallated product was not observed after 30 min (FIG. 8, line b).

Example 3. Hydrolysis of the [Ru]—Cl Complex (1) to [Ru]—H$_2$O (2)

Figure 9:
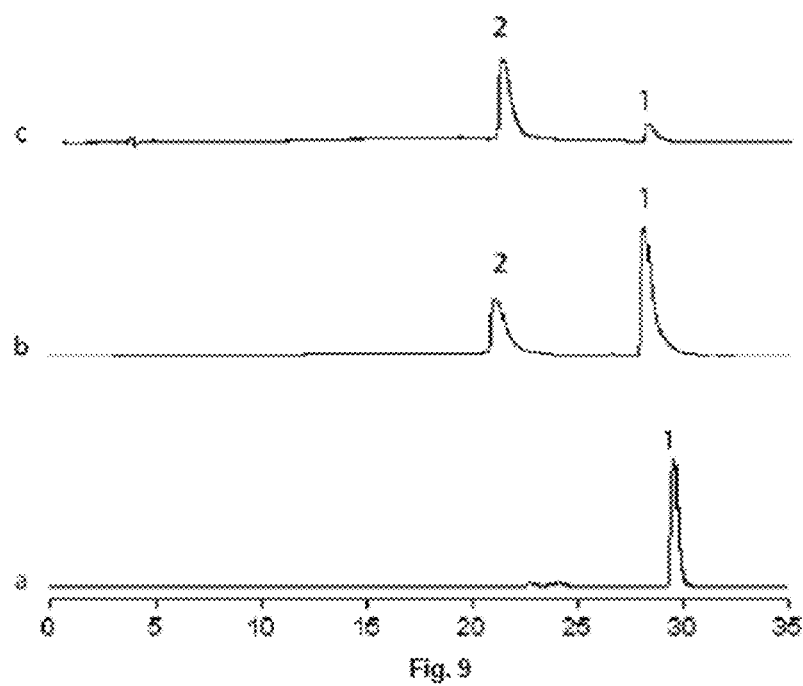
FIG. 9. HPLC chromatograms for complex 1 (250 μM) in 10 mM phosphate buffer (pH=7.5) and 100 mM NaCl at room temperature: (a) in the dark at t=0; (b) after 30 min in the dark; (c) the same mixture after 30 min of irradiation at 455 nm. Eluent: ACN/H$_2$O gradient 2, in the presence of TEAA. $\lambda_{obs}$=222 nm.
Figure 10:
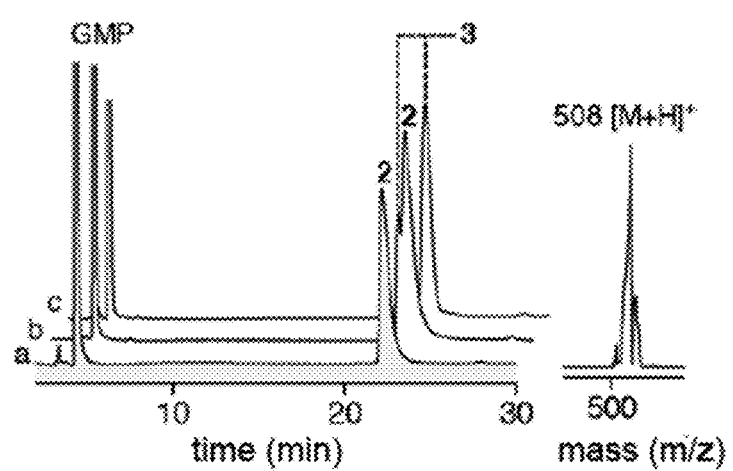
FIG. 10. HPLC chromatograms for the reaction of complex 2 (250 μM) and GMP (750 μM) in 10 mM phosphate buffer (pH=7.5) and 100 mM NaCl at room temperature: (a) in the dark at t=0; (b) after 30 min in the dark; (c) initial mixture after 30 min of irradiation at 455 nm. Eluent: ACN/H$_2$O gradient 2, in the presence of TEAA. $\lambda_{obs}$=222 nm.

It was observed that complex 1 (250 µM) in 10 mM phosphate buffer (pH=7.5) and 100 mM NaCl evolved slowly to the aquo 2 derivative in the dark. This hydrolysis is significantly accelerated by means of irradiation ($\lambda$=455 nm), given that complete conversion was observed after 30 min (FIG. 9, line c). The reaction of the aquo 2 derivative (250 µM) with 3 equivalents of GMP (750 µM) in 10 mM phosphate buffer (pH=7.5) and 100 mM NaCl in the dark gave rise to a conversion of 63% after 30 min (FIG. 10, line b). Irradiation with light ($\lambda$=455 nm) accelerated the process, giving rise to complete conversion after 30 min (FIG. 10, line c).

Example 4. c-MYC Expression Level Determination

Materials and Methods

Cell Cultures

The cell lines were cultured in DMEM supplemented with 10% (v/v) of FCS (fetal calf serum, Gibco), penicillin (100 U/mL), and streptomycin (100 U/mL). The cell cultures were kept in 5% CO$_2$, humidity, and at 37° C.

Real Time Quantitative PCR (qRT-PCR)

$3\times10^5$ HeLa cells (cervical cancer cell line) or Vero cells (renal epithelial cell line) per well were seeded in 6-well plates. After one day, the compounds being assayed were added to the cell culture medium and the cells were incubated for 16 h or 48 h. The total RNA was extracted with a commercial kit (Qiagen RNeasy Mini Kit) following manufacturer's recommendations. The RNA was quantified in a Nanodrop ND-1000. Identical amounts of RNA were used in qRT-PCR (Promega GoTaq 1-Step RT-qPCR System) in CFX96 Real Time System equipment (Bio-Rad). The primers used were: c-MYC: sense: 5'-CTG AGG AGG AAC AAG AAG ATG AG-3' (SEQ ID NO:2), antisense: 5'-TGT GAG GA GGT TTG CTG TG-3' (SEQ ID NO:3); ALAS: sense: 5'-GTT TGG AGC AAT CAC CTT CG-3' (SEQ ID NO:4), antisense: 5'-ACC CTC CAA CAC AAC AAC AG-3' (SEQ ID NO:5); GAPDH: sense: 5'-GGT GTG AAC CAT GAG AAG TAT GA-3' (SEQ ID NO:6), antisense: 5'-GAG TCC TTC GAT CAC CAC AAA G-3' (SEQ ID NO:7)

Western Blot

HeLa cells were incubated to a confluence of 50% in the presence of the indicated concentrations of the assayed agents for 16 h. The cells were lysed in SDS-PAGE Laemmli buffer and subjected to SDS-PAGE and Western blot according to standard methods. The c-MYC protein was detected by means of an anti-MYC antibody (Santa-Cruz Biotechnologies). To detect the signal of the immunoreactive protein, a chemiluminescence method was followed (ECL, Amersham Biosciences).

ICP-MS (Inductively Coupled Plasma Mass Spectrometry)

HeLa cells were seeded in 6-well plates at a density of $3\times10^5$ cells per well. On the next day, complex 1 was added to the cell culture medium in a concentration of 100 µM and the cells were incubated for 16 h. The cells were washed two times with fresh medium and lysed in 70% HNO$_3$/H$_2$O. The samples were diluted to a total volume of 3 mL of water and analyzed by means of ICP-MS (7700x Agilent).

Cytotoxicity (MTT) Assays

Four thousand cells per well were seeded in 96-well plates and incubated for 24 h. Different concentrations of the assayed agents were added to the culture medium and the cells were left in the incubator for another 72 h. MTT was then added at a final concentration of 0.5 mg/ml and incubated for 4 h. The cells were lysed and the formazan precipitates were solubilized by means of adding a volume of a solubilization solution containing 0.1 M HCl and 10% SDS in water. The absorbance was determined at 570 nm in a Tecan Infinito F200 Pro plate reader.

Cell Fractioning

HeLa cells were seeded in 6-well plates at a density of $3\times10^5$ cells per well. On the next day, complex 1 was added to the cell culture medium at a concentration of 100 μM and the cells were incubated for 16 h. The following protocol was followed for nuclear isolation: the cells were washed with PBS and caused to settle by means of centrifugation. They were then resuspended in a cell lysis buffer [HEPES 10 mM; pH=7.5, KCl 10 mM, EDTA 0.1 mM, dithiothreitol 1 mM (DTT), and 0.5% Nonidet-40] and left on ice for 15-20 min, being mixed intermittently. The tubes were vigorously stirred to break the cell membranes and then centrifuged at 12,000 g at 4° C. for 10 min. The integrity of the deposited nuclei was confirmed by means of phase contrast microscopy in Nikon Eclipse TiE equipment. The supernatant fraction containing the cytoplasm and the sediment containing the nuclei were homogenized in 70% $HNO_3/H_2O$ and analyzed by means of ICP-MS as described above. For chromatin extraction, a commercial kit was used (Chromatin Extraction kit, Abcam). The isolated chromatin was resuspended in 70% $HNO_3/H_2O$ and analyzed by means of ICP-MS.

Results

The inventors analyzed the effect of the complexes of the invention on the expression levels of the c-MYC oncogene, both on the messenger expression level and on the protein expression level.

Figure 11:
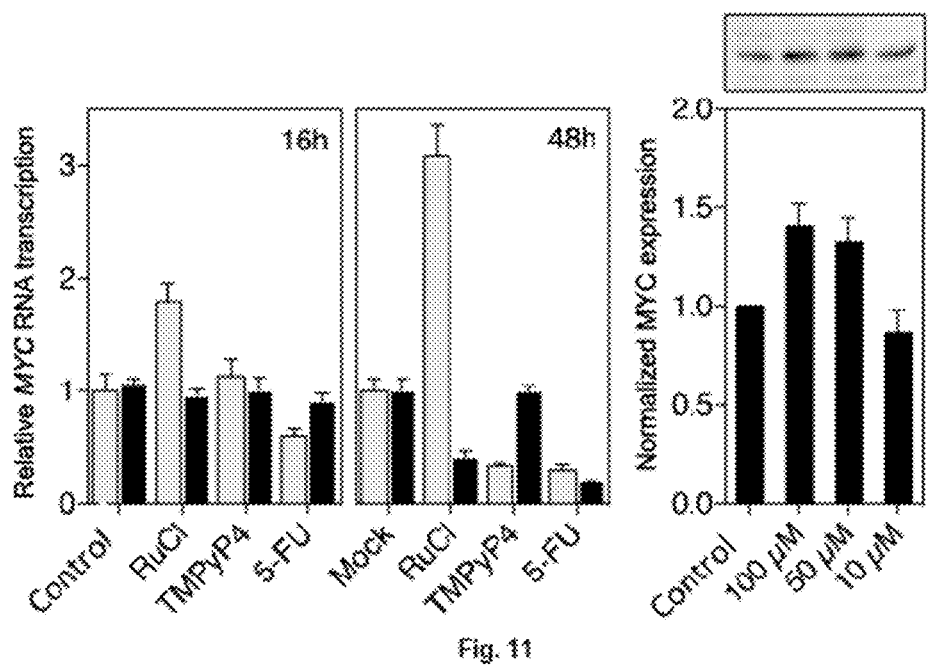
FIG. 11. (Left) Analysis of the expression levels of c-MYC (light colored bars) and ALAS1 (dark colored bars) by means of qRT-PCR. HeLa cells were incubated for 16 h or 48 h with 100 μM of complex 1 (RuCl), TMPyP4, or 50 μM of 5-FU. The levels are expressed in relation to the expression levels of the GAPDH gene. The values are the average of three experiments, and the error bars indicate standard error. (Right) Analysis of the expression of c-MYC by means of Western blot. HeLa cells were incubated for 16 h with 100 μM of complex 1 (RuCl) and then lysed, and c-MYC was detected by means of SDS-PAGE followed by Western blot with an anti-MYC antibody (right, upper panel). The relative amount of protein in two independent experiments was quantified by means of densitometry (right, lower panel). The data is represented as the factor of change with respect to untreated controls. The error bars indicate the standard deviation of the factor of change with respect to untreated controls.
Figure 12:
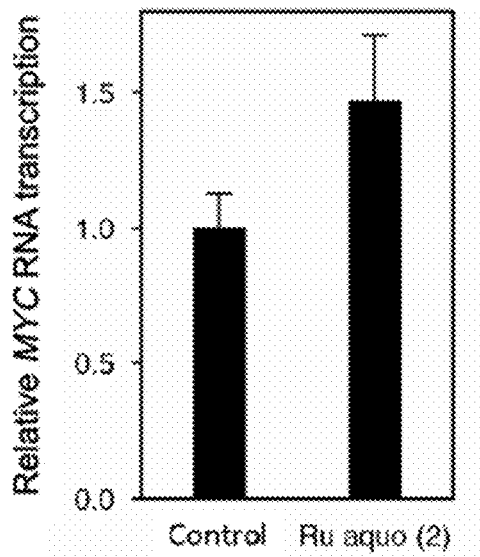
FIG. 12. Analysis of the expression levels of c-MYC by means of qRT-PCR. Vero cells were incubated for 16 h with 100 μM of complex 2 (aquo). The relative levels are expressed in relation to the expression levels of GAPDH. The results correspond to the mean values of three experiments, and the error bars indicate the standard deviation.

FIGS. 11 and 12 show the data of messenger RNA expression in HeLa and Vero cells, respectively. Porphyrin TMPyP4, a compound which binds to guanine quadruplexes and inhibits c-MYC expression was used as control.

As shown in FIG. 11, the HeLa cells treated with complex 1 (100 μM) in DMEM showed a moderate but significant increase in c-MYC transcription with respect to untreated cells (80% at 16 h and 200% at 48 h). As anticipated, alternative treatment with TMPyP4 led to a 60% decrease in the cellular c-MYC mRNA levels after 48 h.

FIG. 11 shows the data of c-MYC protein expression. As observed in relation to the messenger levels, treatment of cells with complex 1 at a concentration of 100 μM, gave rise to a notable increase in the levels of c-MYC (FIG. 11, an average increase of 40%).

This data confirms that, unlike most quadruplex-targeting agents, complex 1 promotes an increase instead of a decrease in gene expression level, thereby acting as a transcriptional activator.

ICP-MS analysis of the isolated nuclei and chromatin obtained after treatment with complex 1 confirmed the presence of relatively significant amounts of ruthenium, in accordance with an efficient cell uptake and nuclear transport of the complexes, as can be seen in Tables 1 and 2 below.

TABLE 1

ICP analysis of cell extracts

| Sample | Concentration (μg/L) | Relative standard deviation |
|---|---|---|
| Blank (20% $HNO_3$) | 0.0190 | 8.8148 |
| Control cells | 0.0955 | 9.9068 |
| Cells treated with complex 1 | 50.1941 | 1.9250 |

TABLE 2

ICP analysis of cell extracts

| | | Ru concentration (pmol) | Relative standard deviation |
|---|---|---|---|
| Complex 1 | Chromatin | 29.49 | 11.95 |
| | Nucleus | 59.45 | 21.39 |
| | Cytoplasm | 290.03 | 106.95 |
| Control | Chromatin | 1.85 | 1.46 |
| | Nucleus | 1.87 | 1.27 |
| | Cytoplasm | 9.39 | 6.34 |

Figure 13:
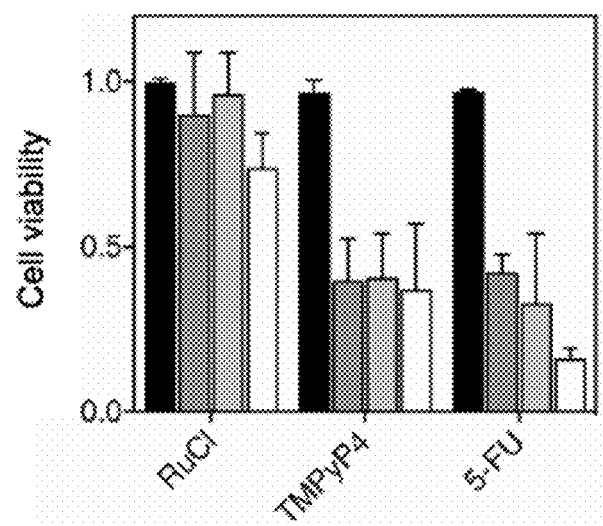
FIG. 13. Viability assay of different cell lines treated with complex 1 (RuCl). The immortalized Vero cell line (white bars), the A549 cell line (light gray bars), and the HeLa cell line (dark gray bars) were incubated for 3 days with 100 μM of RuCl or TMPyP4, or 50 μM of 5-FU. Cell viability was analyzed by means of using a standard MTT assay. The values represent the factor of change with respect to untreated cells (black bars) and are the average result of three different experiments, each of them being performed in triplicate. The error bars represent the standard deviation.

Moreover, the cell viability assays confirmed that complex 1 is essentially non-cytotoxic (FIG. 13).

Figure 14:
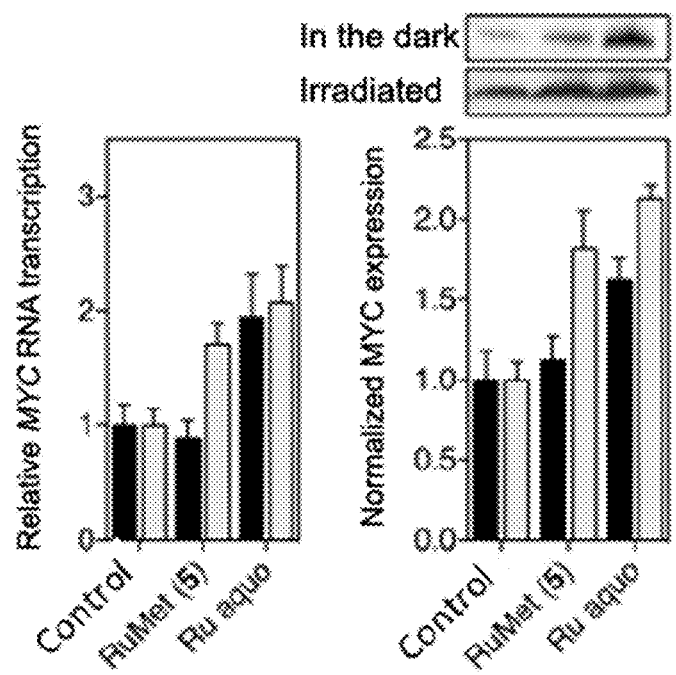
FIG. 14. (Left) Transcription levels of c-MYC determined by means of qRT-PCR in the dark (black bars) or after irradiation (60 min, white bars). HeLa cells were incubated for 16 h with 100 μM of complex 5 (RuMet) or complex 2 (aquo). The expression values are relative to the expression of the GAPDH gene. (Right) Expression levels of c-MYC protein determined by means of Western blot in the presence or absence of complex 5. The relative amount of protein with respect to the expression levels of β-actin was quantified by means of densitometry (lower panel). The experimental method was similar to the one described in FIG. 11.
Figure 15:
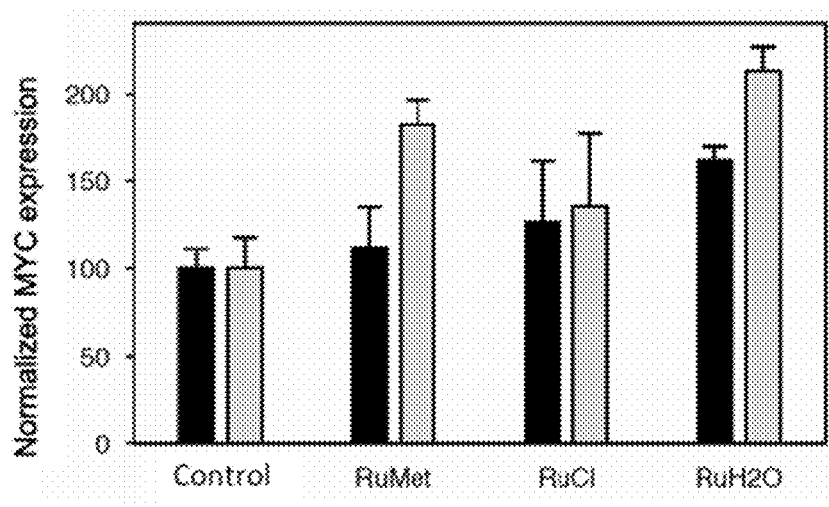
FIG. 15. Expression levels of c-MYC protein determined by means of Western blot in the presence or absence of complex 5 (RuMet), complex 1 (RuCl), or complex 2 (aquo). The light colored bars correspond to expression levels of c-MYC under irradiation conditions whereas the dark colored bars correspond to darkness conditions. The expression of c-MYC is represented as the factor of change with respect to the expression in untreated samples. The relative levels of protein with respect to the expression levels of β-actin were quantified by means of densitometry.
Figure 16:
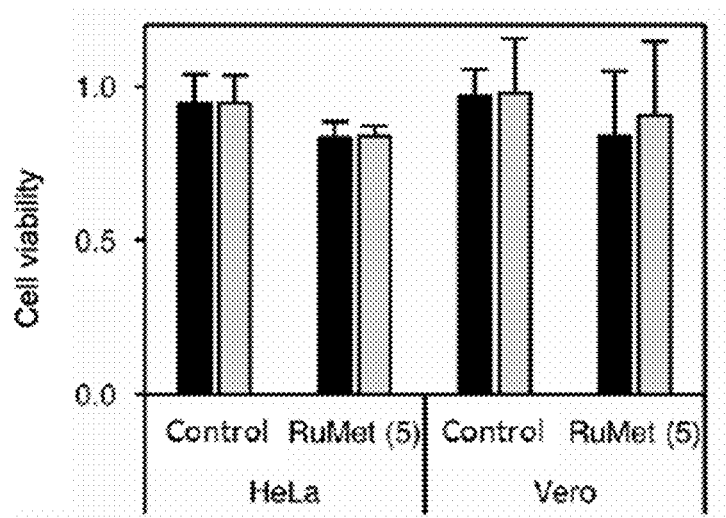
FIG. 16. Viability assay of different cell lines treated with complex 5 (RuMet). The Vero and HeLa cell lines were incubated for 3 days with 100 μM of complex 5. Cell viability was analyzed by means of using a standard MTT assay. The light gray bars indicate the experimental values under irradiation conditions and the black bars indicate the values determined in the dark. The values represent the factor of change with respect to untreated cells in the dark (control) and are the mean of three different experiments, each being performed in triplicate. The error bars represent standard deviation.

In relation to the light-activated complexes (complex 5), qRT-PCR analysis of the expression of messenger RNA of the c-MYC gene showed that RNA levels increased after irradiation, being similar to those observed with complex 2 (aquo). The Western blot protein expression analysis confirmed that the increase of c-MYC protein expression took place in the presence of light, and that the protein levels did not change in the dark (FIGS. 14 and 15). Moreover, complex 2 is active both in the dark and upon being irradiated. Additional experiments confirmed the absence of effect on cell viability due to radiation (FIG. 16).

Example 5. Assays in Cancer Stem Cells of the Pancreas

Pancreatic adenocarcinoma is a pancreatic cancer with a heterogeneous population of tumor cells, including a subpopulation of cancer stem cells (CSCs).

The inventors isolated CSCs and non-CSCs from 6 patient-derived primary tumors by means of FACS (fluorescence-activated cell sorting"). High throughput RNA sequencing (RNAseq) was carried out. RNAseq analysis for the CSC population in comparison with the corresponding non-CSC population generated a list of target genes based on common elements and their differential expression. Among negatively regulated genes, c-MYC was identified as being considerably downregulated in the subCSC population in 6 tumors. It must be highlighted that a downregulation of c-MYC is contrary to what has been commonly characterized for c-MYC in various tumors. However, the inventors have discovered that the expression of c-MYC is differentially regulated in CSCs in comparison with the more differentiated equivalents thereof.

Figure 17:
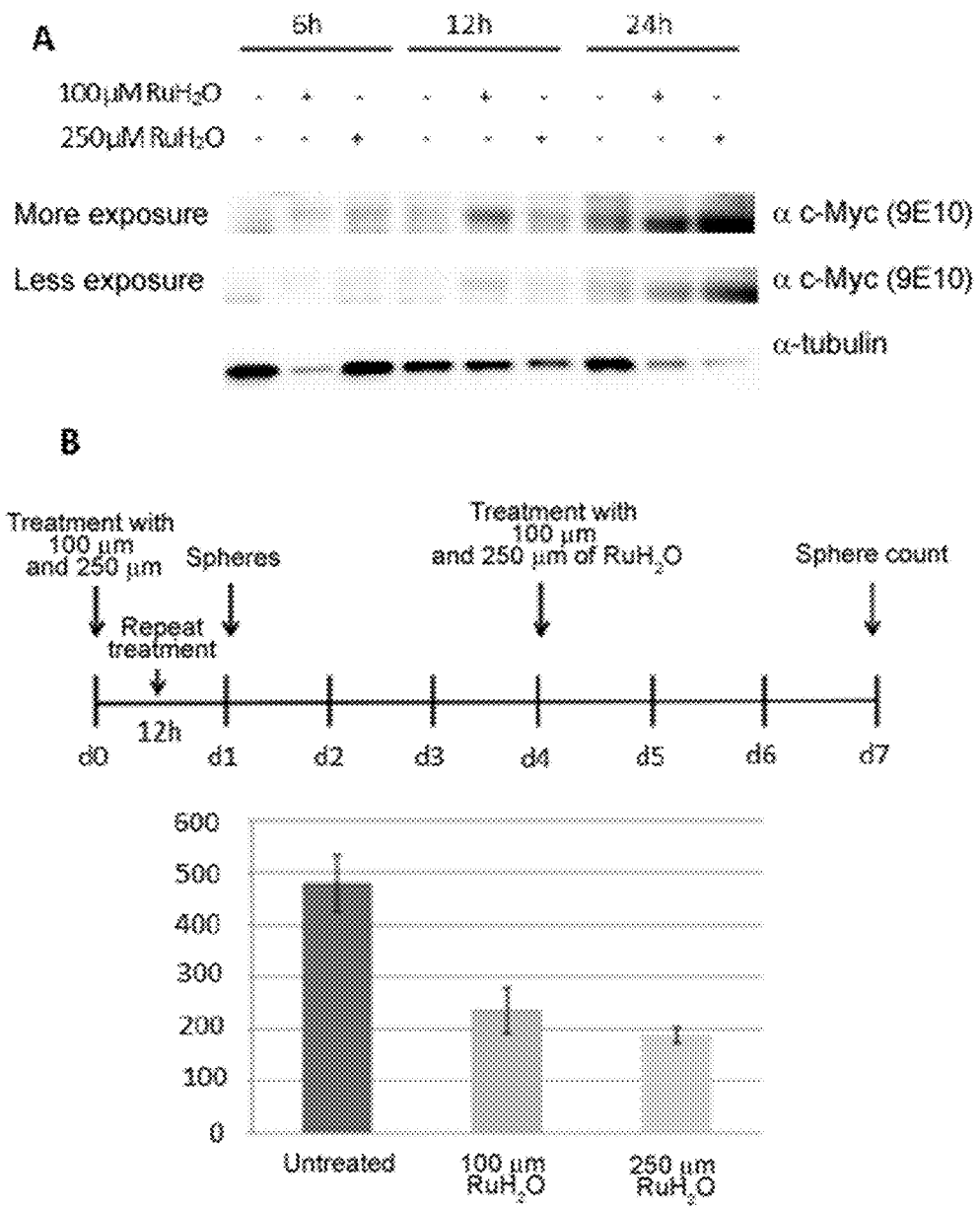
FIG. 17. Effects of complex 2 (RuH$_2$O) on pancreatic ductal adenocarcinoma (PDAC) cells. (A) Complex 2 (RuH$_2$O) increases the expression of c-MYC in PDAC cells, as determined by means of Western blot, in PDACs treated with different concentrations of complex 2 and for different times. (B) Complex 2 (RuH$_2$O) reduces the self-renewal capacity of PDAC cancer stem cells. The upper panel shows the experimental design. The lower panel shows the quantification of the number of spheres/mL determined on day 7 after seeding per treatment group.

On one hand, the inventors analyzed if complex 2 may increase c-MYC expression in pancreatic CSCs, and on the other hand, if the increase in c-MYC expression would negatively affect the CSC phenotype, for example, CSC self-renewal capacity. For this purpose, pancreatic ductal adenocarcinoma (PDAC) cells established from patient-derived xenografts with a low number of passes were cultured, treated with ruthenium complex 2 ($RuH_2O$) at a concentration of 100 and 250 µM for 6, 12, or 24 hours, and c-MYC protein expression was evaluated by means of Western blot. FIG. 17(A) shows that the expression of c-MYC increased after treatment and that the effect was the most prominent 24 hours after treatment. After having achieved a substantial increase in c-MYC expression, it was then analyzed if the CSC self-renewal capacity was affected. To that end, briefly the PDAC cells were pre-treated twice with complex 2 (RuH$_2$O) at a concentration of 100 and 250 µM before establishing sphere cultures in ultra adherent plates as described in Cioffi M (Cioffi M et al. 2015 Gut 12: 1936-1948). The spheres were again treated on day 4 after sphere formation. As shown in FIG. 17(B), a significant, dose-dependent reduction in the sphere formation capacity of PDAC cells treated with complex 2 (RuH$_2$O) was observed in comparison with control cultures. This data confirms the inventors' hypothesis that the increase in c-MYC expression creates an intracellular state which has a negative influence on the functional properties of PDAC cancer stem cells, such as self-renewal.

Figure 18:
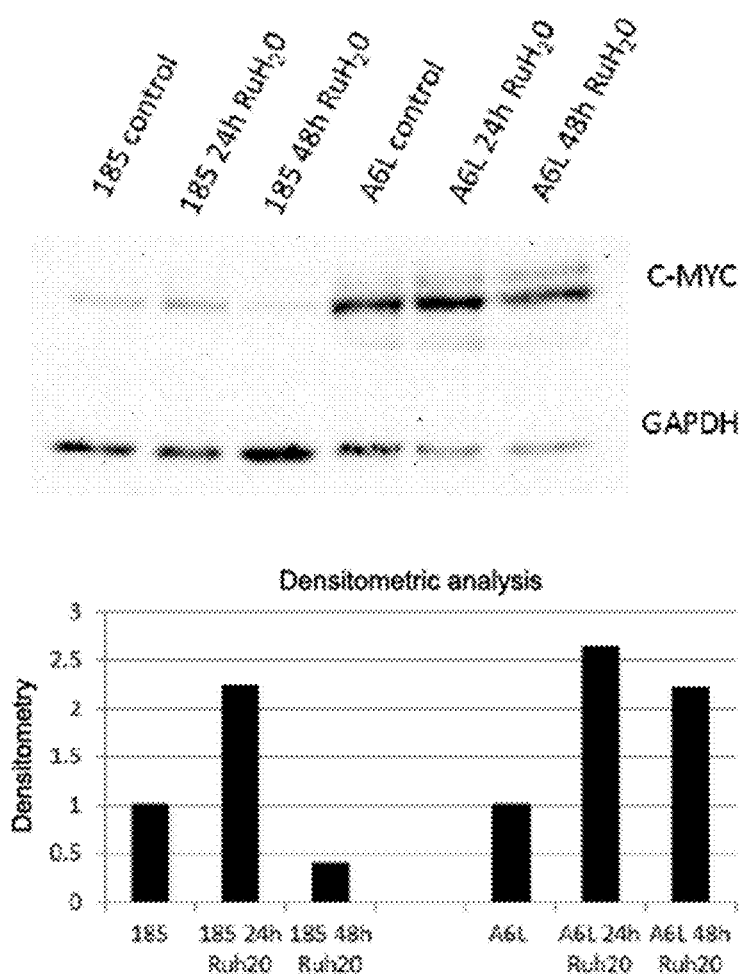
FIG. 18. Effect of RuH$_2$O (250 μM) on the expression of c-MYC and on cell proliferation in adherent PDAC cultures established based on patient-derived xenografts with a low number of passes. Western blot analysis of the expression of c-MYC in cultures 24 and 48 h after treatment with RuH$_2$O.

Using the complexes of the invention, it was tested if RuH$_2$O complex 2 increases c-MYC expression in PDAC adherent cultures established based on patient-derived xenografts with a low number of passes in order to confirm the observations made in HeLa cells. In line with previous observations, treatment of Panc185 and PancA6L cells with 100 µM of RuH$_2$O increased c-MYC protein expression 24 hours after treatment (FIG. 18). The effect was transitory as a significant decrease in c-MYC protein levels was observed 48 hours after treatment.

Figure 19:
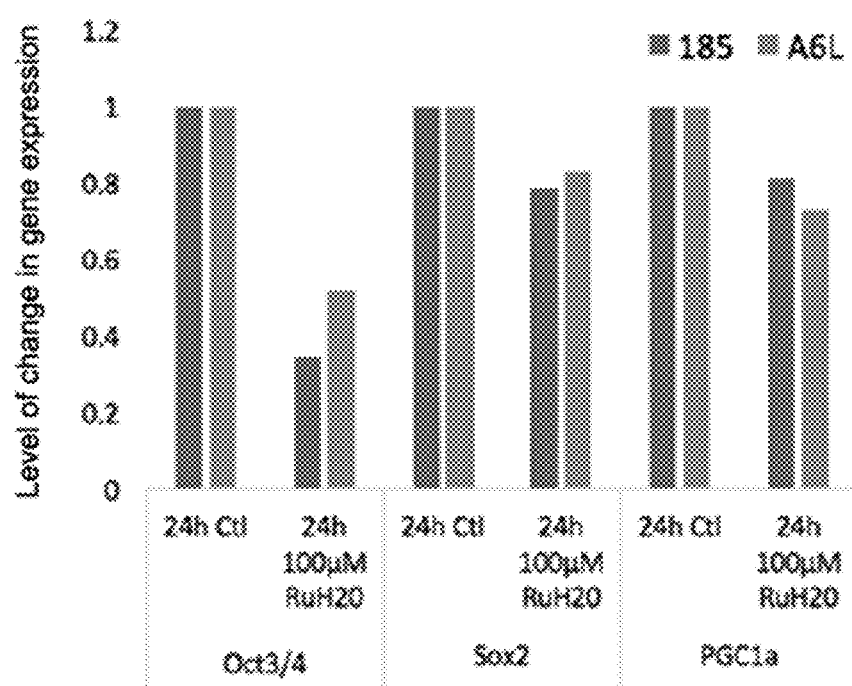
FIG. 19. Effect of RuH$_2$O on gene expression in adherent PDAC cultures established based on patient-derived xenografts with a low number of passes. The RNA of Panc185 and PancA6L cells was extracted 24 hours after treatment with 100 μM of RuH$_2$O. qRT-PCR analysis of Oct3/4, Sox2, and PGC1alpha was performed in cDNA generated from treated samples. The data is normalized to the expression levels of HPRT mRNA. Panc185 cells are also interchangeably referred to herein as 185 and 185 scd and Pacn6AL cells are also interchangeably referred to herein as A6L.

Furthermore, a reduction in PGC1alpha expression, a known c-MYC target, and a reduction in pluripotency-associated genes Oct3/4 and Sox2 were observed after treatment with 100 µM of RuH$_2$O for 24 hours (FIG. 19).

It was then studied if the increased c-MYC expression and the phenotype and transcriptional changes observed were cytotoxic. For this analysis, the ToxiLight™ BioAssay kit, a bioluminescent, non-destructive cytolysis assay kit designed for measuring the adenylate kinase (AK) enzyme released from damaged cells (FIG. 20), was used. Adherent cultures (low in CSC) and cultured spheres (rich in CSC) were treated with increasing doses of RuH$_2$O and cytotoxicity was measured 24, 48, and 72 hours after treatment. In adherent cultures and in both assayed cell lines, toxicity was only observed at 72 hours (3-fold increase in dead cells) when the cells were treated with 250 µM of RuH$_2$O. In contrast, at concentrations of 100 µM, RuH$_2$O induced cell death in spherical cultures, which indicates a selective selection of the CSC population in Panc185 and PancA6L cells.

Figure 21:
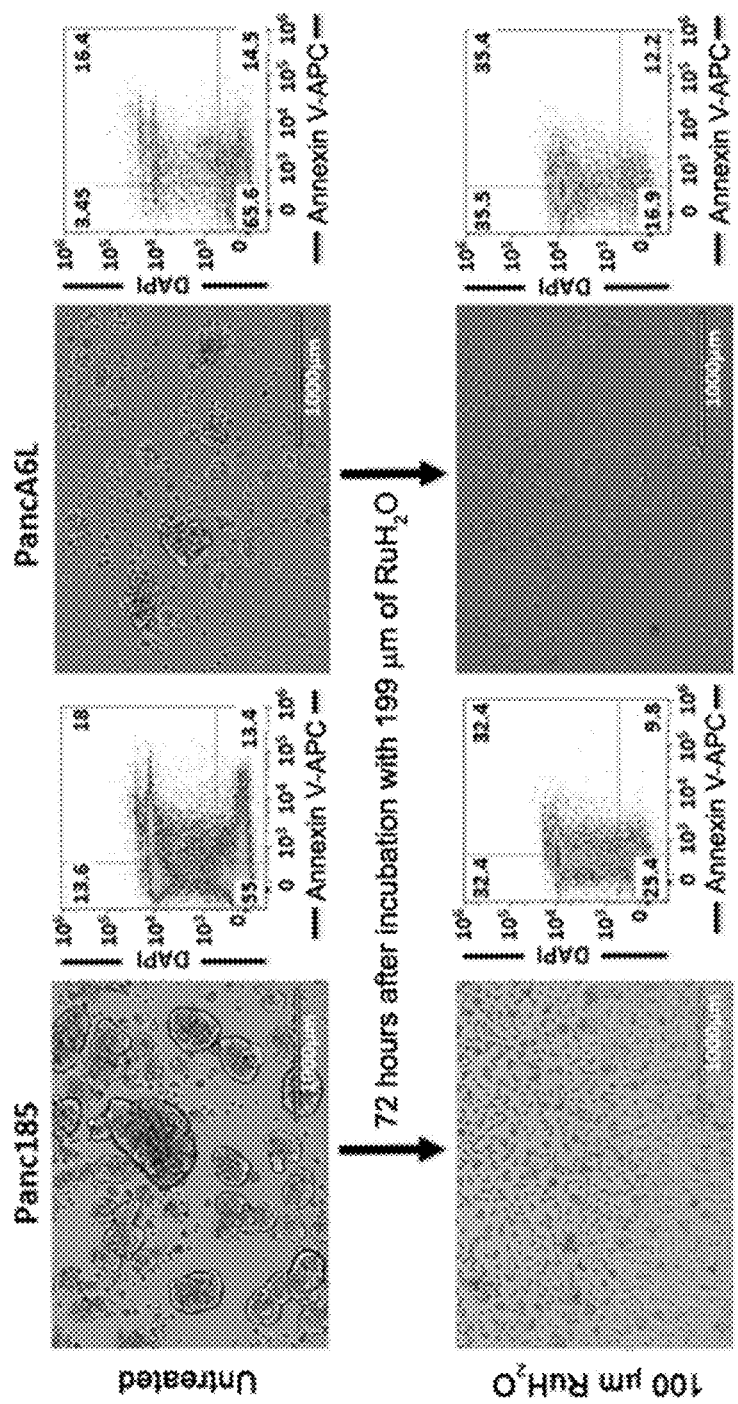
FIG. 21. Cytotoxic effects of RuH$_2$O on PDAC sphere cultures. Light micrographs and annexin-V staining of Panc185 and PancA6L cells after 72 hours of treatment with 100 μM of RuH$_2$O.

The effect of 100 µM of RuH$_2$O on cultures rich in CSC was confirmed at the microscopic level and by measuring annexin V staining. As shown in FIG. 21, spheres treated for 72 hours with 100 µM of RuH$_2$O were visually smaller and apoptotic. Cell viability determined by the percentage of DAPI negative cells dropped by 50%.

Figure 22:
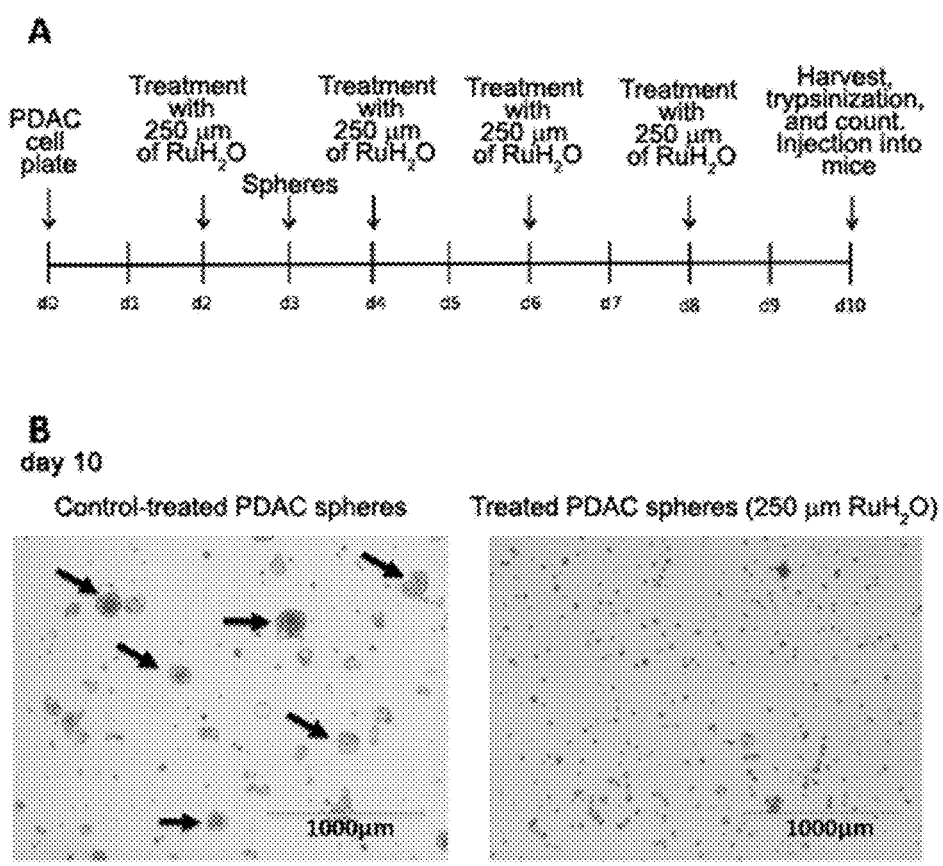
FIG. 22. Effects of RuH$_2$O on PDAC sphere formation. (A) Work sequence of the experiment for evaluating the effect of RuH$_2$O in PDAC CSC (B) Light micrographs of spheres derived from Panc185 and PancA6L cells after 10 days of treatment with 250 μM of RuH$_2$O FIG. 23. Effects of RuH$_2$O on PDAC tumorigenicity in vivo. Panc185 cells were pretreated with RuH$_2$O before subcutaneous injection into NOD-SCID (non-obese diabetic, severe combined immunodeficiency) mice. Tumors were extracted 12 weeks after injection and analyzed. A) Photographs of the tumors extracted from NOD-SCID mice 12 weeks after being injected with 10$^4$ or 10$^3$ Panc185 cells and pretreated with control (CTL) or 250 μM of RuH$_2$O. (B) Summary of the numbers of tumors detected per injection with 10$^4$ or 10$^3$ Panc185 cells and pretreated with control (CTL) or 250 μM of RuH$_2$O. (C) Weights of the tumors extracted from NOD-SCID mice 12 weeks after being injected with 10$^4$ or 10$^3$ Panc185 cells and pretreated with control (CTL) or 250 μM of RuH$_2$O.

It was then evaluated if ruthenium complex 2 may negatively affect CSC phenotypes, such as self-renewal and tumorigenicity. To that end, PDAC adherent cultures established based on patient-derived xenografts with a low number of passes were treated with 250 µM of ruthenium complex 2 (RuH$_2$O) for 24 hours. Treated and untreated cells were trypsinized and sphere cultures were established following the standard protocols (Cioffi M et al. 2015 Gut 12: 1936-1948). The cells were cultured in ultra-low adherent plates for 7 days in serum-free DMEM/F12 supplemented with B27. During these 7 days, the samples were treated again with 250 µM of RuH$_2$O on days 1, 3, and 5 after initiation of the spheres. FIG. 22A shows the work sequence of the aforementioned experiment. As shown in FIG. 22B, a significant reduction in the sphere formation capacity of PDAC cells treated with RuH$_2$O was observed in comparison with the cultures treated with control. The CSC spheres were smaller and less abundant in the RuH$_2$O group.

Figure 23:
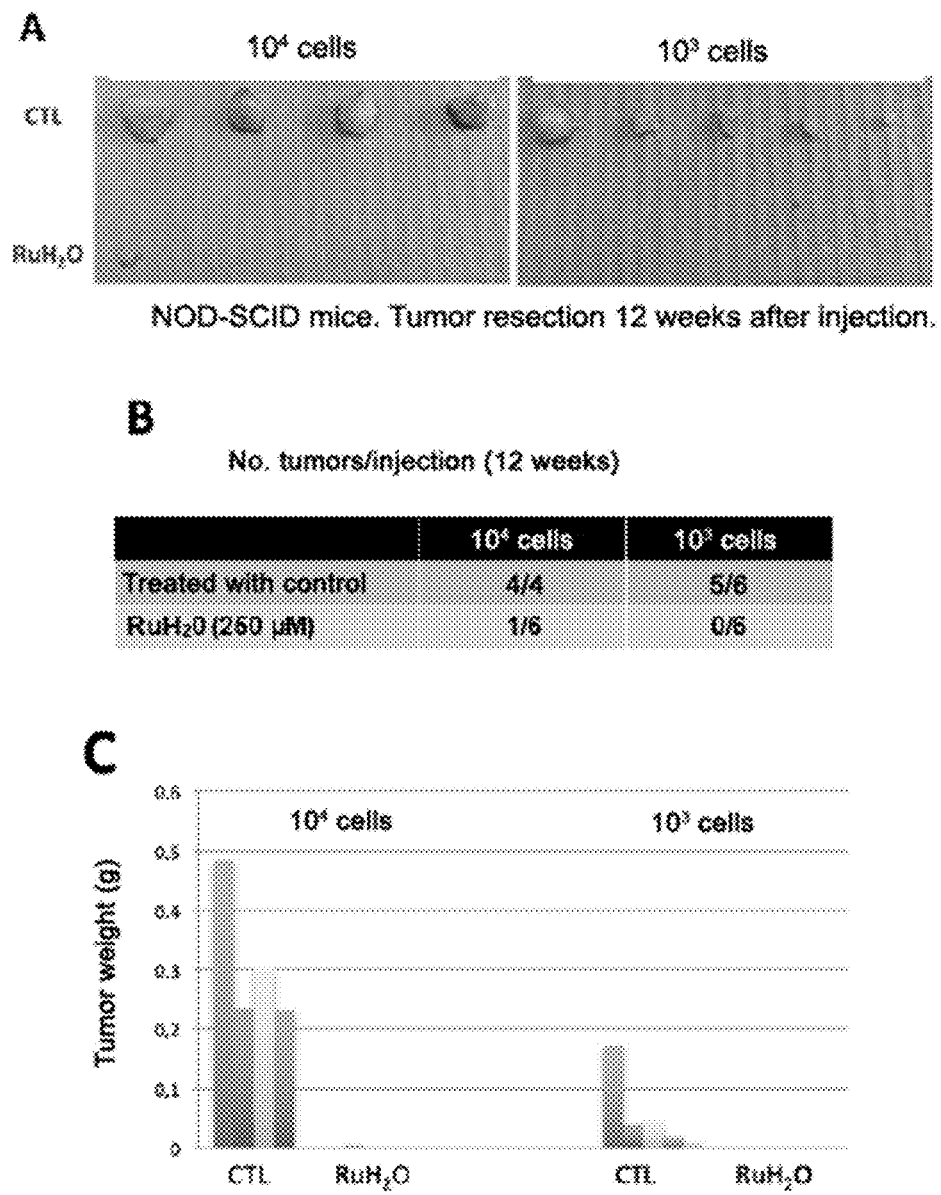

The spheres were then disassociated and equal numbers of control-treated cells and RuH$_2$O-treated cells were injected subcutaneously into immunocompromised NOD-SCID mice to evaluate the tumorigenicity thereof. Twelve weeks after the injection, the tumors were extracted and weighed. FIG. 23A shows the extracted tumors. Treatment with RuH$_2$O significantly reduced the tumor formation capacity of sphere-rich CSCs. While 4 out of 4 injections and 5 out of 6 injections with 10,000 and 1,000 control-treated cells, respectively, led to tumors, only 1 out of every 6 injections with 10,000 RuH$_2$O-treated cells led to tumor. Tumors did not form when 10 times less RuH$_2$O-treated cells were injected (FIG. 23B). Furthermore, the only tumor that developed in the mouse injected with 10,000 RuH$_2$O-treated cells weighed 53 times less than the tumors formed in control-treated mice (0.0058 g with respect to 0.3118 g).

Figure 20:
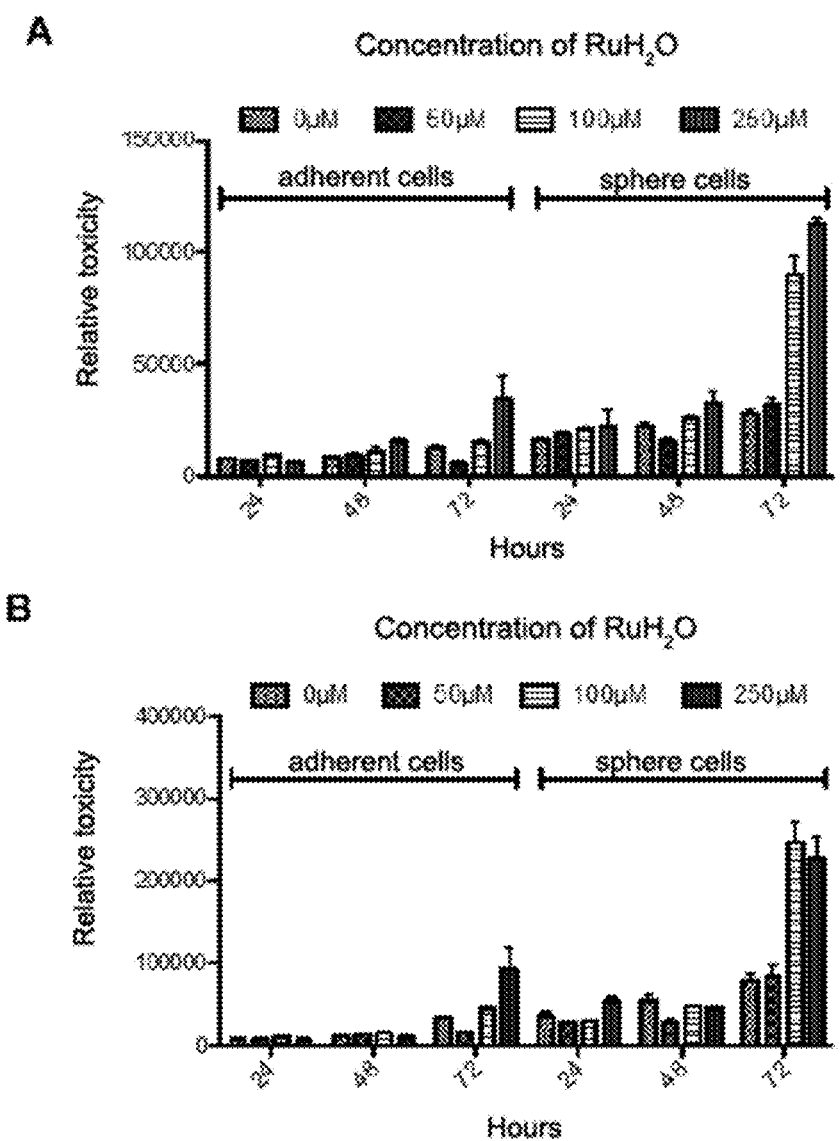
FIG. 20. Cytotoxic effects of RuH$_2$O on PDAC cultures. Relative cell death was determined in adherent cultures (low in CSC) and spheres (rich in CSC) of Panc185 (A) and PancA6L (B) at 24, 48, and 72 hours after treatment with the indicated doses of RuH$_2$O.
Figure 24:
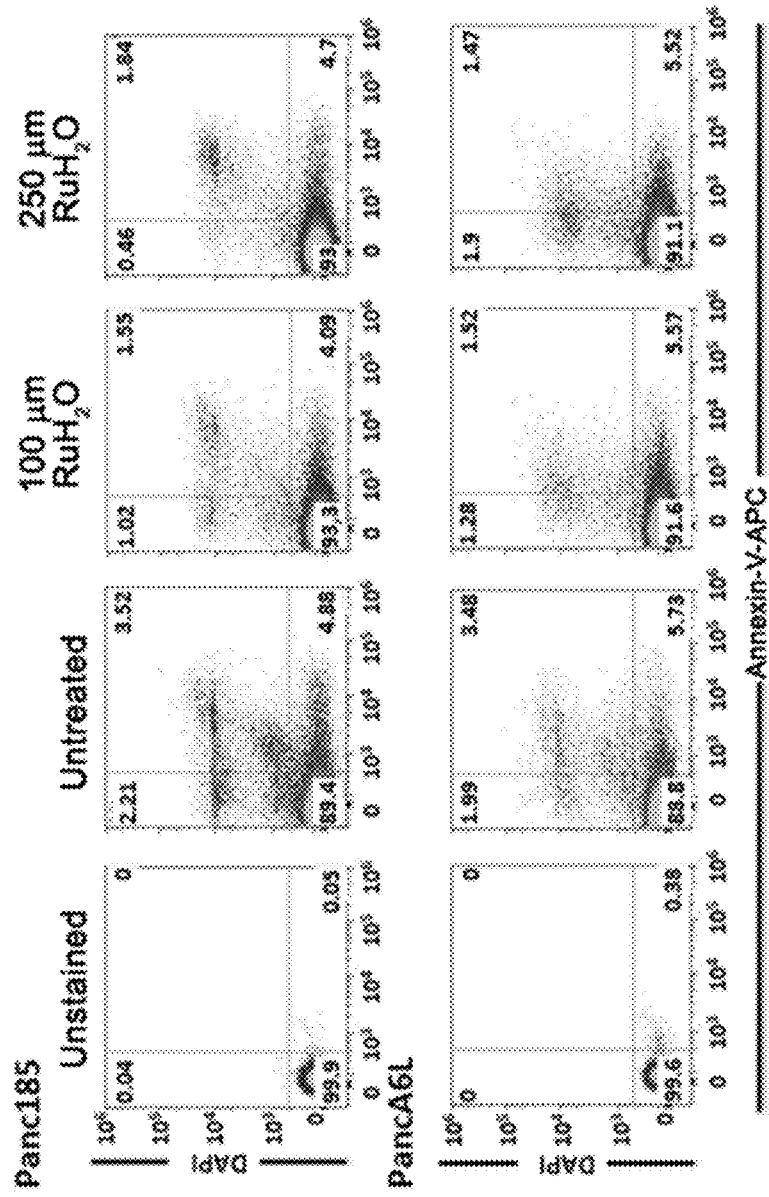
FIG. 24. Induction of apoptosis in PDAC cells. Annexin-V staining of PDAC cells treated for 48 hours with 100 or 250 μM of RuH$_2$O.

To rule out the possibility that the effects mentioned above arise as a result of unspecific cytotoxic effects, adherent cultures (low in CSC) were treated for 48 hours with a single dose of RuH$_2$O (100 or 250 µM) and their subsequent clonogenicity, self-renewal, and tumorigenicity was checked. Under these experimental conditions, no toxicity was observed using the present ToxiLight assay (FIG. 20). PDAC adherent cultures established based on patient-derived xenografts with a low number of passes were treated with 100 or 250 µM of RuH$_2$O for 48 hours. The treated and untreated cells were then trypsinized and the percentage of apoptotic cells was analyzed. In line with the cytotoxicity assays, an increase in the percentage of apoptotic cells was not observed after treatment with 100 or 250 µM of RuH$_2$O (FIG. 24).

Figure 25:
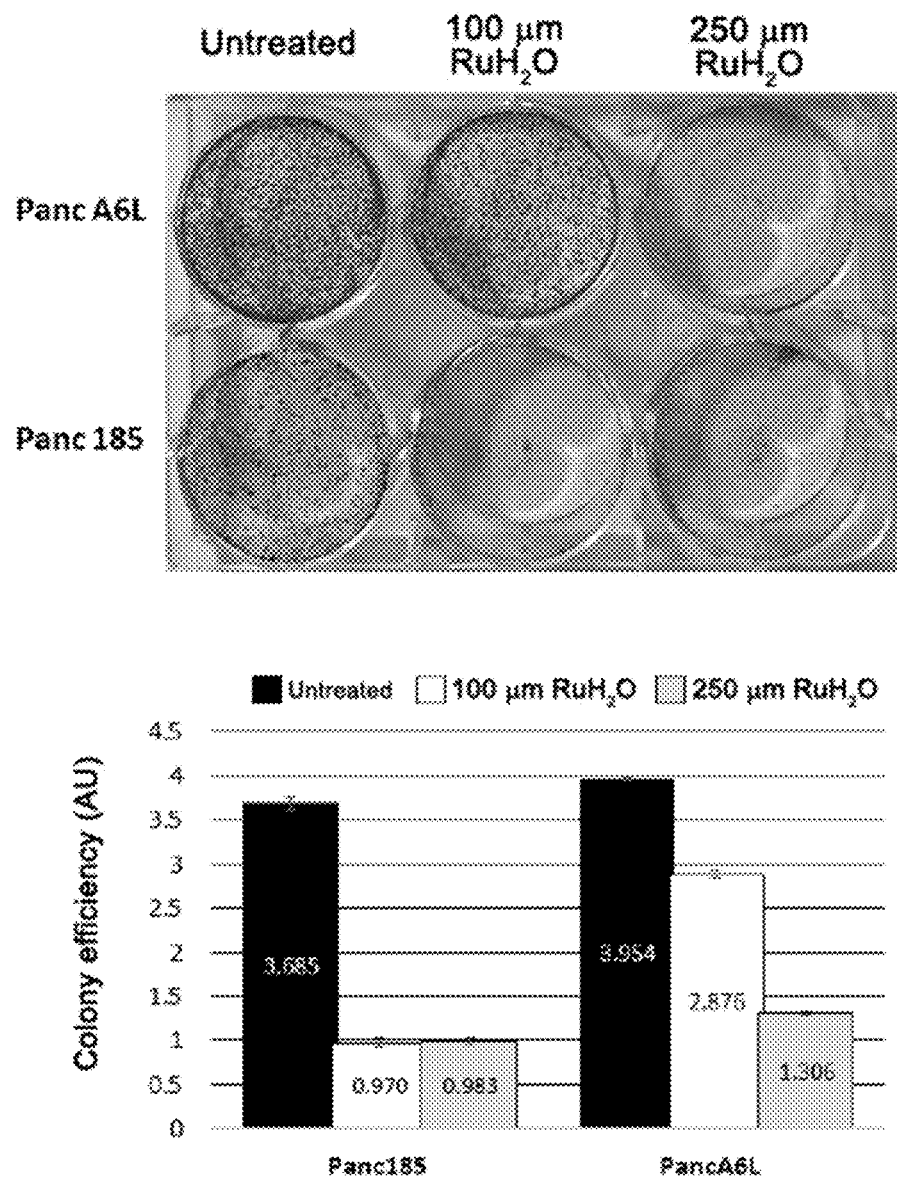
FIG. 25. Clonogenicity of PDAC cells after treatment with RuH$_2$O. (Top) Light micrographs of Panc185 and PancA6L colonies formed after 10 days in culture. The colonies were visualized with crystal violet staining. (Bottom) Colony efficiency quantification. The colonies were lysed in PBS-1% Triton-X and color intensity was measured with a plate reader.
Figure 26:
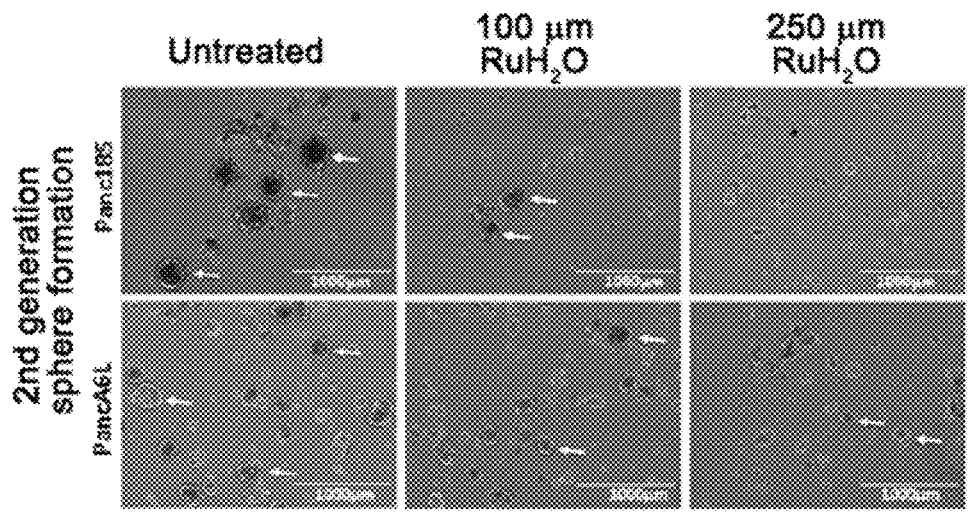
FIG. 26. Sphere formation capacity of PDAC cells after treatment with RuH$_2$O.
Figure 27:
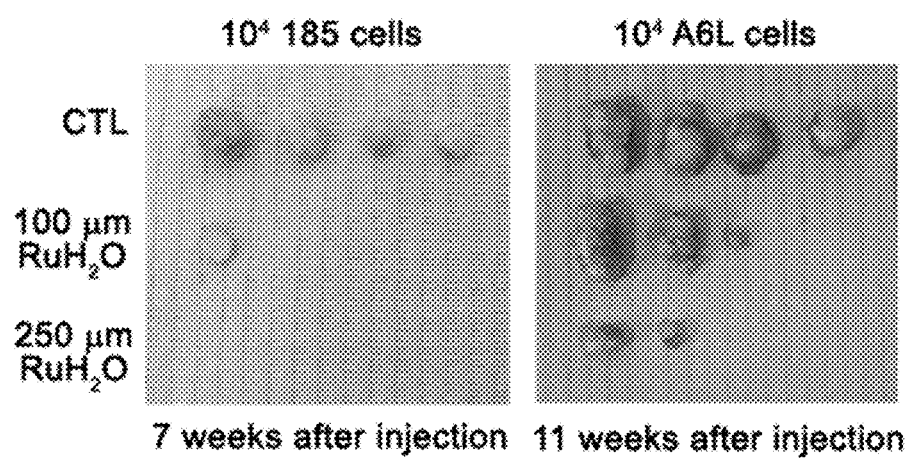
FIG. 27. Tumorigenicity of PDAC cells after treatment with RuH$_2$O. PDAC cells were treated with the indicated concentrations of RuH$_2$O for 48 hours and then injected subcutaneously into NOD-SCID mice. Tumors were extracted 7 or 11 weeks after injection.

The trypsinized cells were then: 1) placed in a plate at a low confluence to evaluate their clonogenicity (FIG. 25); 2) repeatedly cultured in ultra-low adherent plates in serum-free DMEM/F12 supplemented with B27 for intervals of 7 days to evaluate sphere formation capacity over multiple generations (FIG. 26); and 3) subcutaneously injected into NOD-SCID mice to check their tumorigenicity as described above (FIG. 27). All this data clearly shows that treatment with RuH$_2$O prevents clonogenicity, self-regeneration, and tumorigenicity of PDAC cells.

Figure 28:
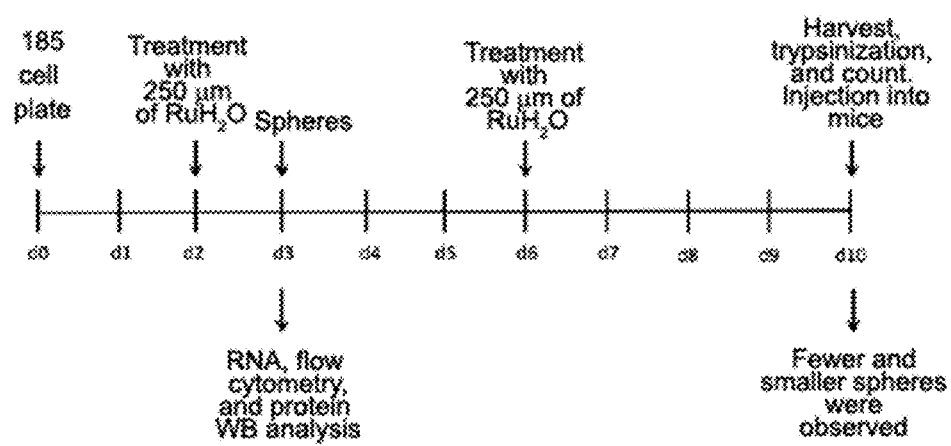
FIG. 28. Work sequence of the experiment for evaluating the effect of the Ru-riboflavin conjugate in PDAC CSC.

Finally, to investigate the capacity of the complexes of the invention to specifically target CSCs, RuH$_2$O was bound to riboflavin through methionine sulfur (conjugate 10) and the cells were treated with this modified compound as described in detail. Again, the PDAC adherent cultures established based on patient-derived xenografts with a low number of passes were treated with 250 µM of Ru-riboflavin. To activate the ruthenium complex, the cells were treated with visible light to release and activate RuH$_2$O. Twenty-four hours after treatment, the treated and untreated cells were trypsinized and sphere cultures were established following the standard protocols (Cioffi M et al. 2015 Gut 12: 1936-1948). The cells were cultured in ultra-low adherent plates for 7 days in serum-free DMEM/F12 supplemented with B27. On day 3 after initiation of the spheres, the cells were again treated with 250 µM of Ru-riboflavin. FIG. 28 shows the work sequence of the experiment.

Figure 29:
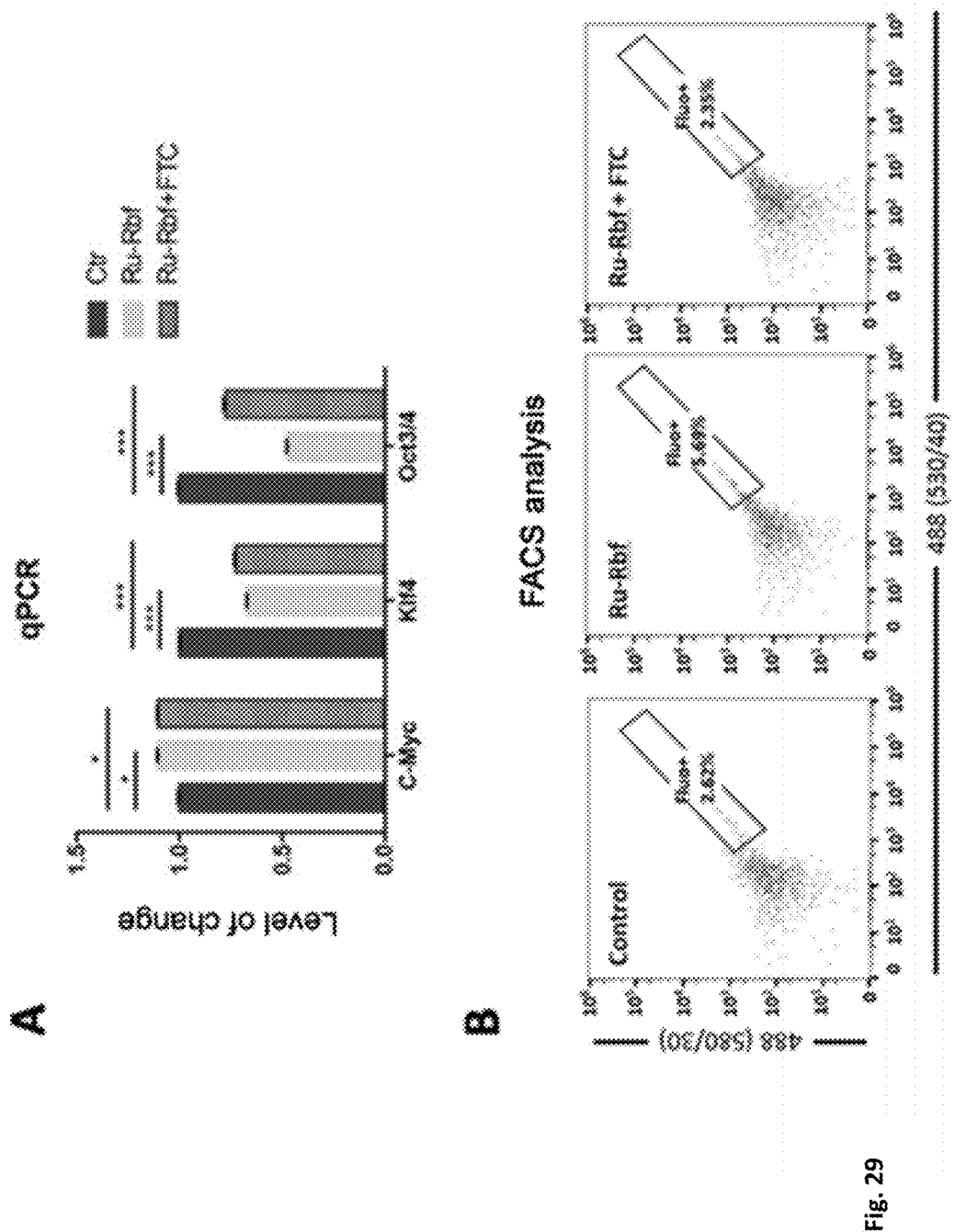
FIG. 29. Effect of Ru-riboflavin conjugate (RuRbf) (250 μM) on gene expression and the self-fluorescence of PDAC CSC. (A) The RNA of Panc185 cells was extracted 24 hours after treatment with control (Ctr), 250 μM of Ru-Rbf, or 250 μM of Ru-Rbf plus FTC. qRT-PCR analysis of C-MYC, Klf4, and OCT3/4 was performed in cDNA generated from treated samples. The data is normalized to the expression levels of HPRT mRNA. (B) Self-fluorescence measurement by means of flow cytometry.

Furthermore, the cells were also treated with fumitremorgin C (FTC), a specific ABCG2 inhibitor. After the first treatment and activation with Ru-riboflavin, a qRT-PCR analysis was performed to evaluate cMYC mRNA levels, as well as the expression of known CSC-related genes, such as the pluripotency-associated genes Klf4 and Oct3/4. Cells treated with Ru-riboflavin in the presence or absence of FTC showed an increase in cMYC RNA levels and a decrease in Klf4 and Oct3/4 CSC-related transcripts (FIG. 29A). To confirm that Ru-riboflavin was capable of accumulating in CSCs, self-fluorescence was measured by means of flow cytometry in cells treated with Ru-riboflavin for 24 hours and an increase in the population of self-fluorescent CSC, that could revert back with FTC (FIG. 29B), was observed.

Figure 30:
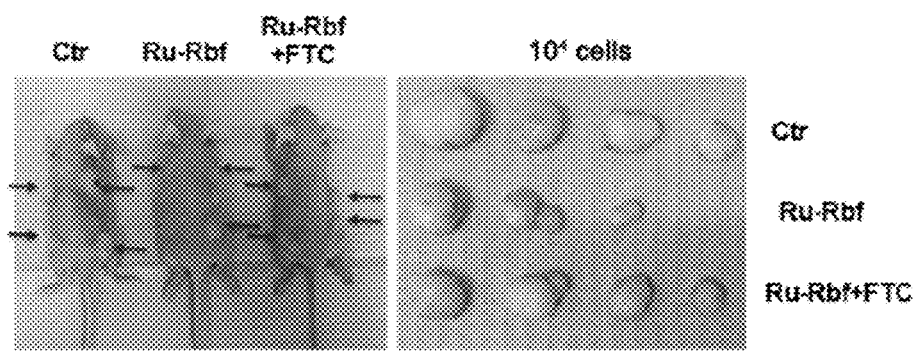
FIG. 30. Effect of Ru-riboflavin conjugate (250 μM) on tumorigenesis of PDAC CSC.

Finally, the tumorigenicity of sphere-rich CSCs was studied as described above. The analysis of the extracted tumors showed a trend towards tumor reduction and proliferation for Ru-riboflavin-treated cells in comparison with the control- and Ru-riboflavin/FTC-treated cells (FIG. 30).

The invention claimed is:

1. A method of treating cancer, where the cancer is a cancer comprising cancer stem cells which comprises contacting said cancer stem cells with a pharmaceutical composition comprising a therapeutically effective amount of a ruthenium complex of formula (I)

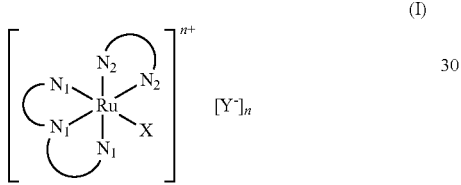

wherein
$N_1$—$N_1$—$N_1$ represents an N,N,N-tridentate aza-aromatic ligand;
$N_2$—$N_2$ represents an N,N-bidentate aza-aromatic ligand;
X is $OH_2$;
$Y^-$ is a monovalent anion; and
n is 2,
wherein the method increases c-MYC protein expression, wherein the therapeutically effective amount is effective to reduce tumorigenicity in cancer stem cells without being cytotoxic to differentiated cancer cells.

2. The method according to claim 1, wherein $N_1$—$N_1$—$N_1$ is selected from the group consisting of:

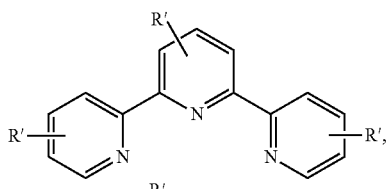

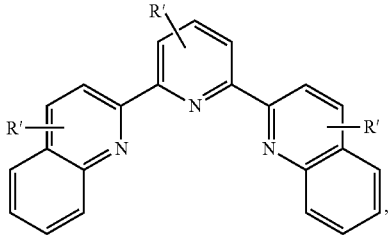

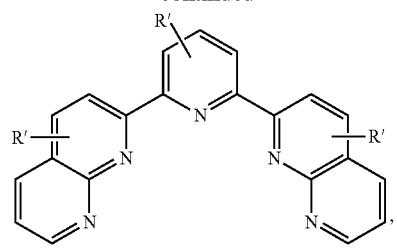

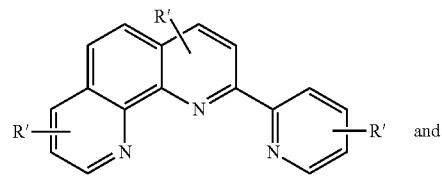

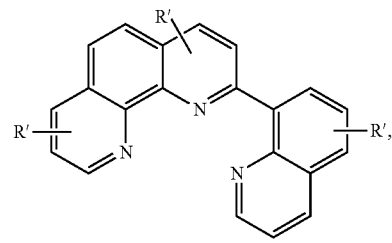

wherein each group R' is independently selected from hydrogen, optionally substituted $C_1$-$C_6$ alkyl, optionally substituted $C_6$-$C_{14}$ aryl, optionally substituted 5- to 10-membered heteroaryl, and halogen.

3. The method according to claim 1, wherein $N_2$—$N_2$ is selected from the group consisting of:

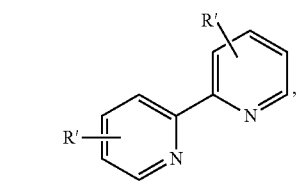

-continued

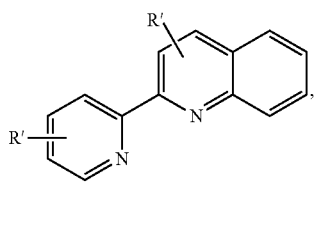

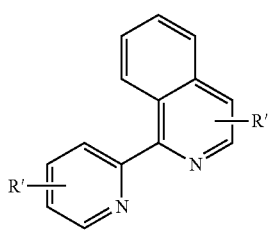

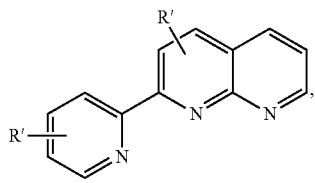

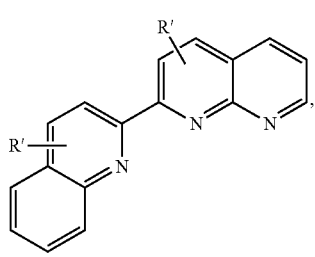

-continued

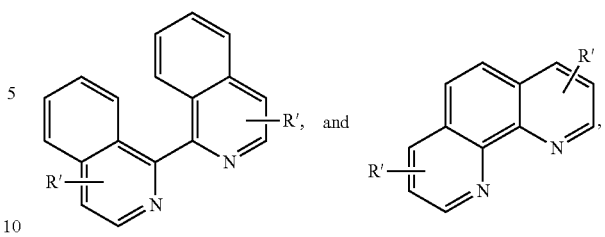

wherein each group R' is independently selected from hydrogen, optionally substituted $C_1$-$C_6$ alkyl, optionally substituted $C_6$-$C_{14}$ aryl, optionally substituted 5- to 10-membered heteroaryl, and halogen.

4. The method according to claim 1, wherein $N_1$—$N_1$—$N_1$ is

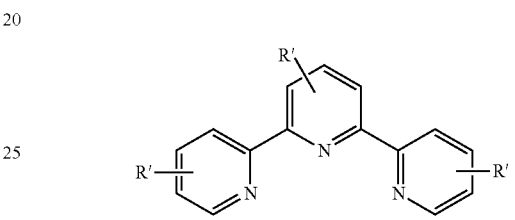

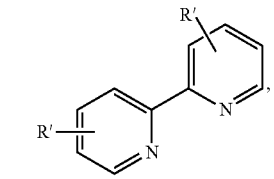

where each group R' is independently selected from hydrogen, optionally substituted $C_1$-$C_6$ alkyl, optionally substituted $C_6$-$C_{14}$ aryl, optionally substituted 5- to 10-membered heteroaryl, and halogen.

5. The method according to claim 1, wherein the ruthenium complex has the following formula:

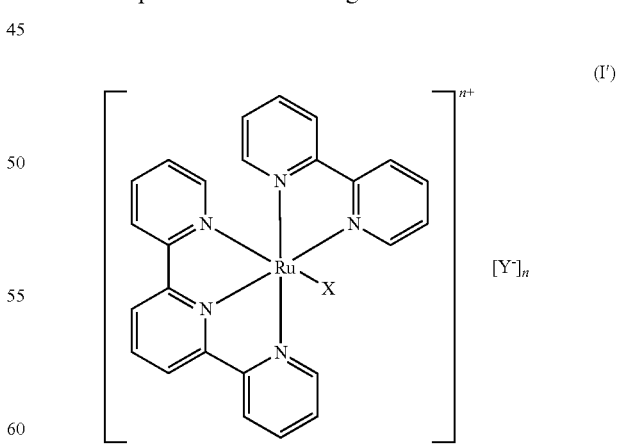

(I')

wherein
X is $OH_2$;
$Y^-$ is a monovalent anion; and
n is 2.

6. The method according to claim 1, wherein the ruthenium complex is

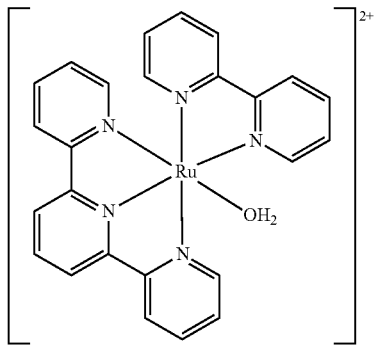

wherein Y⁻ is a monovalent anion.

7. The method according to claim 1, wherein the cancer is selected from the group consisting of breast cancer, lung cancer, colon cancer, prostate cancer, ovarian cancer, pancreatic cancer, cervical cancer, and kidney cancer carcinoma.

8. The method according to claim 7, wherein the cancer is pancreatic adenocarcinoma.

9. A method of treating cancer, where the cancer is a cancer comprising cancer stem cells, which comprises contacting said cancer stem cells with a pharmaceutical composition comprising a therapeutically effective amount of a conjugate comprising:
  a ruthenium complex of formula (I), as defined in claim 1, and
  an ABCG2 substrate or an anti-tumor drug,
  wherein the method increases c-MYC protein expression, and
  wherein the therapeutically effective amount is effective to reduce tumorigenicity in cancer stem cells without being cytotoxic to differentiated cancer cells.

10. The method according to claim 9, where the ABCG2 substrate is selected from the group consisting of imatinib, gefitinib, flavopirodol, topotecan, irinotecan, SN-38, mitoxantrone, cimetidine, prazosin, statins, zidovudine, estrone, 17β-estradiol, protoporphyrin IX, 2-amino-1-methyl-6-phenylimidazo[4,5-b]pyridine, amsacrine, asparaginase, azathioprine, bisantrene, bleomycin, busulfan, capecitabine, carboplatin, carmustine, chlorambucil, cisplatin, cladribine, clofarabine, cyclophosphamide, cytarabine, dacarbazine, dactinomycin, daunorubicin, docetaxel, doxorubicin, epirubicin, etoposide, flavopiridol, fludarabine, fluorouracil, gemcitabine, idarubicin, ifosfamide, irinotecan, hydroxyurea, leucovorin, liposomal daunorubicin, liposomal doxorubicin, lomustine, chlormethine, melphalan, mercaptopurine, mesna, methotrexate, mitomycin, mitoxantrone, oxaliplatin, paclitaxel, pemetrexed, pentostatin, procarbazine, satraplatin, streptozotocin, tegafur-uracil, temozolomide, teniposide, thioguanine, thiotepa, treosulfan, topotecan, vinblastine, vincristine, vindesine, SN-38, vinorelbine, riboflavin, D-luciferin, rhodamine 123, pheophorbide a, BODIPY-prazosin, and Hoechst 33342.

11. The method according to claim 9, where the ABCG2 substrate is riboflavin.

12. The method according to claim 9, where the ruthenium complex is a complex of formula (I')

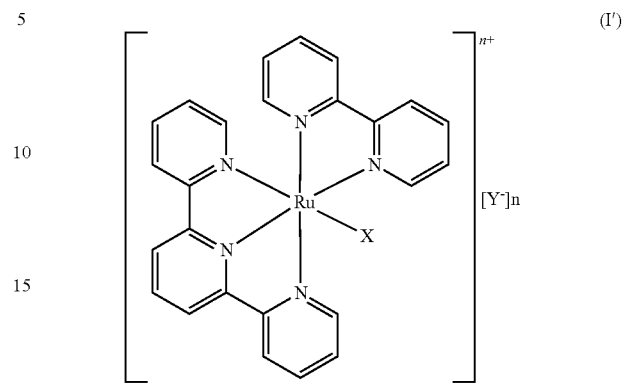

wherein
X is $OH_2$;
Y⁻ is a monovalent anion; and
n is 2.

13. The method according to claim 9, where the conjugate comprises a linker covalently bound to the ruthenium complex and to the ABCG2 substrate or to the anti-tumor drug.

14. The method according to claim 9, wherein the cancer is selected from the group consisting of breast cancer, lung cancer, colon cancer, prostate cancer, ovarian cancer, pancreatic cancer, cervical cancer, and kidney cancer carcinoma.

15. The method according to claim 1, wherein the pharmaceutical composition comprising said therapeutically effective amount of a ruthenium complex of formula (I) further comprises another therapeutic agent.

16. The method according to claim 15, wherein said therapeutic agent is an anti-tumor drug.

17. The method according to claim 1, wherein said increase in c-MYC protein expression is an increase in the dark.

18. The method according to claim 9 wherein the pharmaceutical composition comprising said therapeutically effective amount of the conjugate further comprises another therapeutic agent.

19. The method according to claim 17, wherein said therapeutic agent is an anti-tumor drug.

20. The method of claim 15, wherein the pharmaceutical composition is a combination of two dosage forms.

21. The method of claim 15, wherein the pharmaceutical composition is formulated for simultaneous, separate, or sequential administration.

22. The method of claim 18, wherein the pharmaceutical composition is a combination of two dosage forms.

23. The method of claim 18, wherein the pharmaceutical composition is formulated for simultaneous, separate, or sequential administration.

* * * * *